(12) United States Patent
Toneguzzo et al.

(10) Patent No.: US 9,833,412 B2
(45) Date of Patent: *Dec. 5, 2017

(54) TRIPLE COMBINATION RELEASE MULTI-LAYERED TABLET

(71) Applicant: OSMOTICA KERESKEDELMI ES SZOLGALTATO KFT, Budapest (HU)

(72) Inventors: Fernando G. Toneguzzo, Buenos Aires (AR); Glenn A. Meyer, Wilmington, NC (US); Marcelo A. Ricci, Buenos Aires (AR); Marcelo A. Coppari, Buenos Aries (AR); Ana C. Pastini, Buenos Aires (AR); Gustavo A. Fischbein, Buenos Aires (AR)

(73) Assignee: Osmotica Kereskedelmi es Szolgaltato KFT, Budapest (HU)

(*) Notice: Subject to any disclaimer, the term of this patent is extended or adjusted under 35 U.S.C. 154(b) by 149 days.

This patent is subject to a terminal disclaimer.

(21) Appl. No.: 14/188,150

(22) Filed: Feb. 24, 2014

(65) Prior Publication Data

US 2014/0302141 A1 Oct. 9, 2014

Related U.S. Application Data

(63) Continuation of application No. 12/141,677, filed on Jun. 18, 2008, now Pat. No. 8,685,451, which is a continuation of application No. PCT/CR2006/000008, filed on Dec. 20, 2006.

(60) Provisional application No. 60/754,972, filed on Dec. 29, 2005.

(51) Int. Cl.
*A61K 9/24* (2006.01)
*A61K 9/00* (2006.01)

(52) U.S. Cl.
CPC ............ *A61K 9/209* (2013.01); *A61K 9/0004* (2013.01)

(58) Field of Classification Search
None
See application file for complete search history.

(56) References Cited

U.S. PATENT DOCUMENTS

| | | |
|---|---|---|
| 4,576,604 A | 3/1986 | Guittard et al. |
| 4,627,850 A | 12/1986 | Deters |
| 4,801,461 A | 1/1989 | Hamel et al. |
| 4,810,502 A | 3/1989 | Ayer et al. |
| 4,839,177 A | 6/1989 | Colombo et al. |
| 4,999,226 A | 3/1991 | Schock et al. |
| 5,057,321 A | 10/1991 | Edgren et al. |
| 5,093,200 A | 3/1992 | Watanabe et al. |
| 5,128,145 A | 7/1992 | Edgren et al. |
| 5,162,117 A | 11/1992 | Stupak et al. |
| 5,190,763 A | 3/1993 | Edgren et al. |
| 5,192,550 A | 3/1993 | Edgren et al. |
| 5,221,536 A | 6/1993 | Edgren et al. |
| 5,342,627 A | 8/1994 | Chopra et al. |
| 5,395,626 A | 3/1995 | Kotwal et al. |
| 5,474,786 A | 12/1995 | Kotwal et al. |
| 5,558,879 A | 9/1996 | Chen et al. |
| 5,681,583 A | 10/1997 | Conte et al. |
| 5,681,584 A | 10/1997 | Savastano |
| 5,738,874 A | 4/1998 | Conte et al. |
| 5,968,554 A | 10/1999 | Beiman et al. |
| 6,004,582 A | 12/1999 | Faour et al. |
| 6,183,778 B1 | 2/2001 | Conte et al. |
| 6,217,904 B1 | 4/2001 | Midha et al. |
| 6,217,905 B1 | 4/2001 | Edgren et al. |
| 6,238,699 B1 | 5/2001 | Rubin |
| 6,294,200 B1 | 9/2001 | Conte et al. |
| 6,340,476 B1 | 1/2002 | Midha et al. |
| 6,372,255 B1 | 4/2002 | Saslawski et al. |
| 6,521,255 B2 | 2/2003 | Vergez et al. |
| 6,544,554 B1 | 4/2003 | Maeda et al. |
| 6,555,136 B2 | 4/2003 | Midha |
| 6,569,456 B2 | 5/2003 | Faour et al. |
| 6,572,890 B2 | 6/2003 | Faour et al. |
| 6,599,532 B2 | 7/2003 | Faour et al. |
| 6,605,302 B2 | 8/2003 | Faour et al. |
| 6,613,357 B2 | 9/2003 | Faour et al. |
| 6,660,299 B2 | 12/2003 | Conley et al. |
| 6,756,056 B2 * | 6/2004 | Rubin ........................ 424/464 |
| 8,685,451 B2 | 4/2014 | Toneguzzo |
| 2002/0058061 A1 | 5/2002 | Midha et al. |
| 2002/0128251 A1 | 9/2002 | Storm et al. |

(Continued)

FOREIGN PATENT DOCUMENTS

| | | | |
|---|---|---|---|
| AR | WO2004/087116 A2 * | 10/2004 | ............ A61K 31/00 |
| JP | 10-053524 | 2/1998 | |
| WO | WO99/17745 | 4/1999 | |
| WO | WO00/15197 | 3/2000 | |
| WO | WO00/59479 | 12/2000 | |
| WO | WO03/105809 | 12/2003 | |
| WO | WO2004/087095 | 10/2004 | |
| WO | WO2004/087116 A2 | 10/2004 | |

*Primary Examiner* — Dennis Heyer
(74) *Attorney, Agent, or Firm* — Rick Matos; Innovar, L.L.C.

(57) ABSTRACT

This invention pertains to a multi-layered tablet for a triple combination release of active agents to an environment of use. More particularly, the invention pertains to a multi-layered tablet (1) comprising two external drug-containing layers (2 and 3) in stacked arrangement with respect to and on opposite sides of an oral dosage form (4) that provides a triple combination release of at least one active agent. In one embodiment of the invention the dosage form is an osmotic device. In another embodiment of the invention the dosage form is a gastro-resistant coated core. In yet another embodiment of the invention the dosage form is a matrix tablet. In a different embodiment the dosage form is a hard capsule.

20 Claims, 18 Drawing Sheets

(56) References Cited

U.S. PATENT DOCUMENTS

| | | |
|---|---|---|
| 2003/0031707 A1 | 2/2003 | Rubin |
| 2003/0035839 A1 | 2/2003 | Hirsh et al. |
| 2003/0092724 A1 | 5/2003 | Kao et al. |
| 2003/0143272 A1* | 7/2003 | Waterman .................... 424/471 |
| 2003/0170181 A1 | 9/2003 | Midha et al. |
| 2003/0194439 A1 | 10/2003 | Midha et al. |
| 2003/0224045 A1 | 12/2003 | Han et al. |
| 2003/0228360 A1 | 12/2003 | Han et al. |
| 2004/0115265 A1 | 6/2004 | Benkerrour et al. |
| 2004/0166159 A1 | 8/2004 | Han et al. |
| 2004/0186184 A1 | 9/2004 | Berlin |
| 2004/0253311 A1 | 12/2004 | Berlin et al. |
| 2005/0025831 A1 | 2/2005 | Lam et al. |
| 2005/0163851 A1 | 7/2005 | Feleder et al. |
| 2006/0062851 A1 | 3/2006 | Vergez et al. |
| 2006/0063810 A1* | 3/2006 | Vergez et al. ................ 514/321 |
| 2006/0127478 A1 | 6/2006 | Zerbe et al. |
| 2007/0077301 A1 | 4/2007 | Meyer et al. |
| 2008/0175909 A1 | 7/2008 | Vergez et al. |
| 2008/0299197 A1 | 12/2008 | Toneguzzo et al. |

\* cited by examiner

TRIPLE COMBINATION RELEASE MULTI-LAYERED TABLET

CROSS-REFERENCE TO EARLIER FILED APPLICATIONS

This application claims the benefit of and is a continuation of U.S. Ser. No. 12/141,677 filed Jun. 18, 2008, now U.S. Pat. No. 8,685,451 B2, issued Apr. 1, 2014, which claims the benefit of and is a continuation of PCT International Application No. PCT/CR2006/00008 filed Dec. 20, 2006, which claims the benefit of U.S. Provisional Application No. 60/754,972 filed Dec. 29, 2005, the entire disclosures of which are hereby incorporated by reference.

FIELD OF THE INVENTION

This invention pertains to a multi-layered tablet for a triple combination release of active agents to an environment of use. More particularly, the invention pertains to a multi-layered tablet comprising two external drug-containing layers in stacked arrangement with respect to and on opposite sides of an oral dosage form that provides a triple combination release of at least one active agent.

BACKGROUND OF THE INVENTION

Multi-layered tablets that provide different release profiles for one or more different drugs are known.

U.S. Pat. No. 4,999,226 to Schock et al. discloses a multi-layered tablet having two different drug-containing layers separated by a layer comprising a pharmaceutically inert excipient. The inert layer provides a barrier layer between the drugs layers, in order to solve the problems associated with the physical and chemical incompatibilities between the drugs.

U.S. Pat. No. 5,342,627 to Glaxo Canada Inc. discloses a device for the release of at least one active substance into a fluid medium by dissolution comprising a covering, which is impermeable to the active substance and the fluid, or is swellable or slowly soluble in said fluid, having at least one aperture therein and defining a shaped cavity, the cavity being filled by a shaped core comprising the active substance. The covering composition is compressed onto a pre-shaped core of active substance. The geometric configuration of the compression-coated core controls the release profile of drugs. The device may be provided with an outer soluble coating which provides an initial delay before release of active substance begins, or alternatively provides an immediate dose of active substance.

The U.S. Pregrant Patent Application Publication No. 20020128251 to GlaxoSmithKline discloses a layered tablet formulation comprising an immediate release layer and a slow release layer. The layered tablet may have two layers, or two layers plus one or more barrier layer, as well as a coating layer. The coating layer may itself contain active material content, and may, for example, be an immediate release layer, which immediately disintegrates in contact with water or aqueous media to release its active material content.

U.S. Pregrant Patent Application Publication No. 20040115265 to Bristol Meyers Squibb discloses a multi-layered tablet that includes two drug-containing layers separated by a middle barrier layer to minimize interaction of the drugs.

U.S. Pat. No. 6,660,299 to Beecham Pharmaceuticals Limited discloses a multi-layered tablet consisting of a slow release layer, a rapid release layer and optionally a barrier layer, which may be located between the respective first and second layers, and/or on one or more of the outer surfaces of the first and second layers, for example the end faces of the layers of a substantially cylindrical tablet. The tablet consisting of an immediate release and a slow release layer can be optionally coated with a coating layer. The barrier layer is designed to retain sufficient physical integrity at least until complete or substantially complete release of drug.

SCOLR Pharma, Inc. (Bellevue, Wash.) has filed an application with the United States Patent Office on an Asymmetrical Multiple Layered Tablet for Controlled Release. The technology is reportedly designed to work with single or multiple ingredients and/or drugs, allowing those ingredients/drugs to be programmed for release at pre-selected rates and/or at pre-selected regions within the body.

SkyPharma offers the GEOMATRIX™ combination tablet, which is a bimodal release multi-layered tablet made by compression. The GEOMATRIX™ tablet comprises two opposing barrier layers that module release of drug from a middle layer to provide controlled release of drug from the middle layer (Conte et al., *Pharm. Technol.* 22, No. 3, 174-82, 1998). This technology is further described in U.S. Pat. No. 4,839,177 to Jagotec AG.

U.S. Pat. No. 5,738,874, U.S. Pat. No. 6,183,778, and U.S. Pat. No. 6,294,200 to Jagotec AG disclose multi-layered tablet formulations.

The SMARTRIX™ combination tablet (www.smartrix.com) is a bimodal release multi-layered tablet having a controlled release drug-containing layer, containing a first drug, placed between two stacked rapidly eroding layers, either one or both of which contains a different second drug. The middle layer has a biconcave surface whereas the upper and lower layers have a convex layer that mates with the middle layer and an outer flat surface. The shape of the surface(s) between the layers can be varied to provide specific drug release profiles from the core.

PCT International Publication No. WO 03/105809 discloses a two-layered tablet containing pioglitazone in immediate release form and metformin in prolonged release form.

PCT International Publication No. WO 03/101431, U.S. Pregrant Patent Application Publication No. 20030092724, and U.S. Pat. No. 6,372,255 disclose a bi-layered tablet having an immediate release layer and a controlled release layer.

Japanese Patent Application No. 1989-287048, French Patent Application No. 1999-0000625, U.S. Pat. No. 5,637,320, and Omori at al. (*Pharm. Tech. Jpn,* 2001, 17(9), pp. 1429-1432, 1435-1441) disclose layered formulations that provide an immediate and slow release of drug.

European Patent Application EP 1260216 discloses a concentrically bi-layered tablet comprising a first portion having at least one discrete outer layer comprising a therapeutically effective amount of at least one pharmaceutically active ingredient capable of intraoral administration, and a second portion located within said first portion that comprises a therapeutically effective amount of at least one pharmaceutically active ingredient capable of oral administration and which is releasable and orally ingestible by the patient after the outer layer has disintegrated or has dissolved intraorally. The second portion can provide immediate release or sustained release of the pharmaceutically active ingredient.

Japanese Patent Application No. 1996-211279 discloses a multi-layered tablet having a variety of different layers.

U.S. Pregrant Patent Application Publications No. 20040253311 and No. 20040186184 disclose a multi-layered tablet having a combination of a decongestant and an anti-histamine.

PCT International Publication No. WO 04/064815 discloses a three-layered tablet having an immediate release layer of famotidine, an immediate release layer of aspirin and a slow release layer of famotidine.

U.S. Pat. No. 5,093,200 discloses a multi-layered tablet having a rapid release layer, a slow release layer and metal stearate layer between the other two layers.

U.S. Pat. No. 5,681,583 discloses a multi-layered tablet having a variety of different layers for rapid, controlled and gradual release.

U.S. Pat. No. 5,395,626 and U.S. Pat. No. 5,474,786 discloses multi-layered particles that comprise concentric coatings to provide immediate and sustained release of drug.

U.S. Pat. No. 5,968,554 to Beiman et al. discloses a delivery system that contains a core comprising an active pharmaceutical, an enteral coating over the core comprising a pH dependent water soluble polymer, a second coating of the active pharmaceutical, and thereafter a coating that is soluble in gastric juices.

U.S. Pat. No. 5,162,117 to Schering Corporation describes a two pulse tablet of flutamide designed to provide an immediate release dose and a second delayed dose in pulsatile manner in the gastrointestinal tract. The first pulse is contained in an immediate release layer while the second pulse is obtained from a core which contains a solid dispersion of the flutamide in a carrier. The pulses are separated by a film layer of an enteric coating at 4-15% weight percent of the core.

U.S. Pat. Nos. 6,238,699 and 6,756,056 disclose an oral antiparkinson drug delivery system consisting of carbidopa and levodopa in immediate and sustained release compartments. An outer layer comprising an immediate release composition comprising carbidopa and levodopa is separated by an intermediate excipient layer from a core layer comprising a sustained release composition comprising carbidopa and levodopa.

Other patents disclosing a controlled release dose form containing levodopa and carbidopa which requires immediate release and controlled release components include U.S. Pregrant Patent Application Publications No. 20030224045, No. 20030228360, No. 20030031707, and No. 20040166159, and the PCT International Publication No. WO 00/15197.

Multi-layered osmotic devices that provide a controlled release of drug from a core and a rapid/immediate release of drug from an external coating are known. U.S. Pat. No. 6,004,582, U.S. Pat. No. 6,521,255, U.S. Pat. No. 6,569,456, U.S. Pat. No. 6,572,890, U.S. Pat. No. 6,599,532, U.S. Pat. No. 6,605,302, U.S. Pat. No. 6,613,357, and the PCT International Publications No. WO04/056335 and No. WO04/087095 to Osmotica Corp. disclose various embodiments of a multi-layered osmotic device, wherein an osmotic core is surrounded by an immediate or rapid release drug-containing composition.

Thombre et al. (*J. Controlled Release* 94(1), 75-89, 2004) disclose an osmotic device having a monolithic, bi-layered or tri-layered core.

U.S. Pat. No. 4,576,604 to Alza Corporation discloses several different embodiments of an osmotic device having a drug in the core and at least one lamina surrounding the core.

U.S. Pat. No. 4,801,461 to Alza Corporation discloses an osmotic dosage form comprising pseudoephedrine in the core, a semipermeable wall surrounding the core comprising varying amounts of cellulose acetate or cellulose triacetate and varying amounts of hydroxypropylcellulose, a passageway in the wall for delivering the drug from the core and, optionally, a lamina on the outside of the wall comprising pseudoephedrine.

U.S. Pat. No. 4,810,502 to Alza Corporation discloses an osmotic dosage form for delivering pseudoephedrine (Ps) and brompheniramine (Br) which comprises a core containing Ps and Br, a wall surrounding the core comprising cellulose acylate and hydroxypropylcellulose, a passageway in the wall for delivering the drug, and a lamina on the outside of the wall comprising Ps, BR, at least one of hydroxypropylcellulose or hydroxypropyl methylcellulose, and poly(ethylene oxide) for enhancing the mechanical integrity and pharmacokinetics of the wall.

U.S. Pat. No. 5,057,321, and U.S. Pat. No. 5,128,145 to Alza Corporation disclose a dosage form comprising a wall surrounding a compartment, the wall comprising at least in part a semipermeable polymeric composition permeable to the passage of fluid and substantially impermeable to the passage of drug, a layer in the compartment comprising a formulation comprising a dosage unit amount of a drug for performing a therapeutic program and a maltodextrin, a layer in the compartment comprising an osmotic formulation for imbibing, and absorbing fluid for expanding in size for pushing the drug maltodextrin formulation from the dosage form, and at least one passageway in the wall for releasing the drug. In one embodiment an immediate release lamina is compressed or air sprayed around the external surface of the delivery device to yield an immediate release coat.

U.S. Pat. No. 5,190,763, U.S. Pat. No. 5,192,550, U.S. Pat. No. 5,221,536 and U.S. Pat. No. 6,217,905 to Alza Corporation disclose a dosage form comprising: a wall surrounding a compartment, the wall comprising at least in part a semipermeable polymeric composition permeable to the passage of fluid and substantially impermeable to the passage of an anti-Parkinson drug; a layer in the compartment comprising a formulation comprising a dosage unit amount of an anti-Parkinson drug for performing a therapeutic program; a layer in the compartment comprising an osmotic formulation for imbibing and absorbing fluid for pushing the anti-Parkinson formulation from the dosage form; and, at least one passageway in the wall for releasing the anti-Parkinson drug. In one embodiment an immediate release lamina is compressed or air sprayed around the external surface of the delivery device to yield an immediate release coat.

U.S. Pat. No. 5,558,879 to Andrx Pharmaceuticals discloses a controlled release tablet for water soluble drugs in which a passageway is formed in the environment of use, i.e., the GI tract of a person receiving the formulation. The controlled release tablet consists of a core, a dual layer membrane coating around the core, and an outer immediate release coating containing a drug and a water soluble polymer.

U.S. Pat. No. 5,681,584 to Alza Corporation discloses a controlled release drug delivery device comprising a core containing a drug, an optional osmotic agent and optional excipients, a delayed release jacket comprising at least one of a binder, an osmotic agent and a lubricant surrounding the core, a semipermeable membrane surrounding the delayed release jacket and optionally having a passageway, a drug containing layer either on the outside of the semipermeable membrane or between the semipermeable membrane and the delayed release jacket, and an optional enteric coat either on the outside of the drug-containing layer, between the drug-containing layer and the semipermeable membrane or on the outside of the semipermeable membrane when the drug-containing layer is between the delayed release jacket and the semipermeable membrane.

U.S. Pregrant Patent Application Publication No. 20050025831 to Alza Corporation discloses an osmotic dosage form comprising a longitudinally compressed tablet core containing a plurality of layers wherein a drug is contained in at least one layer and at least one other layer comprises a suitable fluid-expandable polymer, a semipermeable wall surrounding said longitudinally compressed tablet core to thereby form a compartment having an osmotic gradient to drive fluid from an external fluid environment contacting said semipermeable wall into said compartment, and an orifice formed through said semipermeable wall and into said longitudinally compressed tablet core to permit drug to be released from within said compartment into said external fluid environment. The dosage forms may additionally comprise an immediate-release dose of drug.

U.S. Pat. No. 6,544,554 to Chugai Seiyaku Kabushiki Kaisha discloses a formulation that has a drug core surrounded by a release control layer to present a mechanism by which the drug in the core is rapidly released after a predetermined delay in time. The formulation also has a rapid drug release portion provided outside the release control layer so that the drug can be released more than once at intervals after single dosing. Further in addition, the invention relates to a formulation that incorporates a plurality of drugs in both a core and one or more drug release layers so that different active ingredients can be released at different times.

While the prior art discloses a wide variety of oral multi-layered tablets, none of the prior art discloses a multi-layered tablet for a triple combination release of active agents to an environment of use. Thus, there is a need for a drug delivery system that provides a triple combination release of at least one active agent. Such a system could improve patient compliance to a drug regimen or offer opportunities of treatment otherwise not attainable.

SUMMARY OF THE INVENTION

The present invention seeks to provide an improvement upon the related dosage forms known in the art.

Some embodiments of the invention provide a multi-layered tablet comprising two external drug-containing layers in stacked arrangement with respect to and on opposite sides of an oral dosage form such that the tablet provides a triple combination release of at least one active agent.

Another aspect of the invention provides a multi-layered tablet comprising two external drug-containing layers in stacked arrangement with respect to and on opposite sides of an osmotic device comprising a core coated with a semipermeable membrane having at least one preformed passageway through it.

A combination release tablet comprising: a) a drug-containing rapid release first compressed composition comprising at least one drug; b) a drug-containing extended release second compressed composition comprising at least one drug and a release rate modifier; and c) a preformed and film-coated extended release intermediate drug-containing composition comprising a drug-containing core surrounded by a coating; wherein the first compressed composition and second compressed composition oppose one another, are in direct contact with, in stacked arrangement with respect to, and disposed on opposite faces or surfaces of the intermediate drug-containing composition, whereby the tablet provides three different active agent release profiles.

The preformed and film-coated extended release intermediate drug-containing composition can be an osmotic device comprising a core surrounded by a membrane having a preformed passageway through it. The membrane can be a semipermeable membrane, a microporous membrane, or an impermeable membrane. Depending upon how the osmotic device is manufactured, the preformed passageway may or may not be plugged. When the preformed passageway is plugged by the first or second compressed composition, initial release of drug from the core is delayed for at least a period of about 10 min.

The preformed and film-coated extended release intermediate drug-containing composition can be a capsule comprising a shell enclosing a drug-containing composition. The shell may or may not comprise at least one preformed passageway. The shell can be erodible, swellable, degradable and/or soluble in aqueous medium. The drug-containing composition within the shell optionally comprises a release rate modifier, if not, the shell is a release rate-controlling shell.

The preformed and film-coated extended release intermediate drug-containing composition can be a gastro-resistant coated core comprising a gastro-resistant coating surrounding a drug-containing composition. The core can comprise a release rate-controlling material. A gastro-resistant coated core is adapted for release of drug downstream of the gastric region following oral administration of the tablet to a subject. For example, the gastro-resistant coated core can be adapted for release of drug in the intestine or colon following oral administration of the tablet to a subject.

The multi-layered tablet comprises one drug or two, three, four or more different drugs. At each occurrence, the identity of the drug in a layer is independently selected from any pharmaceutically acceptable drug. For example, each drug-containing composition can comprise a drug different from the drug in any other drug-containing composition present. Alternatively, two drug-containing compositions can comprise the same drug and the third drug-containing compositions can comprise a different drug. In another embodiment, a drug in the first compressed composition is different than a drug in the second compressed composition, optionally, wherein a drug in the first compressed composition is different than a drug in the drug-containing core, optionally, wherein a drug in the second compressed composition is different than a drug in the drug-containing core. In another embodiment, a drug in the first compressed composition is the same as a drug in the drug-containing core. In still another embodiment, the first compressed composition comprises two different drugs, the core comprises a third different drug, and the second compressed composition comprises a charge of either one of the three different drugs. Another embodiment provides the first compressed composition comprising a charge of each of two different drugs, the core comprising a charge of the third different drug, and the second compressed composition comprising an additional charge of either one of the three different drugs. In other embodiments, two or three of the drug-containing compositions comprise the same drug. When two of the drug-containing compositions have the same drug, the third drug-containing composition will have a drug that is the same as or different than the drug in the other two compositions.

Each drug-containing composition can independently comprise more than one drug. For example, a first drug-containing composition can have two different drugs, while the remaining second drug-containing composition can comprise a third different drug or it can comprise a drug that is the same as one of the drugs in the first drug-containing composition.

Another aspect of the invention provides a multi-layered tablet comprising two external drug-containing layers in stacked arrangement with respect to and on opposite sides of a gastro-resistant coated core.

Yet another aspect of the invention provides an oral dosage form that provides a multi-layered tablet comprising two external drug-containing layers in stacked arrangement with respect to and on opposite sides of a hard capsule.

In some embodiments of the invention, the first external drug-containing layer releases the drug in an immediate/rapid form, the second external drug-containing layer releases the drug in an extended form, and the osmotic device, gastro-resistant coated core or hard capsule releases the drug in an extended form.

In other embodiments, the release of the drug from the osmotic core will begin after the preformed passageway is no longer plugged by the external drug-containing layer if the preformed passageway is made before the external drug-containing layers have been formed. The location and size of the preformed passageway in the osmotic device is varied as needed to provide the desired impact upon drug release. In some embodiments, the preformed passageway is adjacent the external extended release layer or the external immediate/rapid release layer. The preformed passageway can be made before or after the external drug-containing layer(s) has (have) been formed. The delayed period for initiation of the release will depend upon whether the preformed passageway is adjacent the immediate/rapid release layer or the extended release layer and upon whether or not the preformed passageway has been formed before or after attachment of the external layer(s).

Other embodiments of the invention include those wherein one of the external drug-containing layers releases the drug in an immediate/rapid form, the other external drug-containing layer releases the drug in an extended form, and the gastro-resistant coated core releases the drug in a delayed and extended form. In other embodiments, one of the external drug-containing layers releases the drug in an immediate/rapid form, the other external drug-containing layer releases the drug in an extended form, and the gastro-resistant coated core releases the drug in a delayed and rapid form.

The external drug-containing layers can be applied onto the intermediate drug-containing formulation by compression.

Combinations of the various embodiments disclosed herein are considered within the scope of the invention. Other features, advantages and embodiments of the invention will become apparent to those skilled in the art by the following description, accompanying examples.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1:
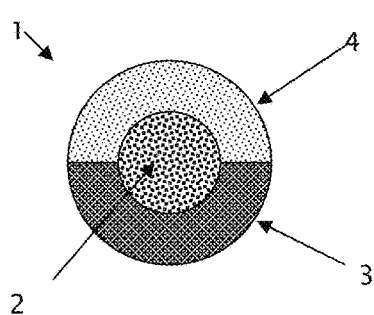
FIG. 1 depicts a cross-sectional view of a multi-layered tablet comprising two external drug-containing layers in stacked arrangement with respect to and on opposite sides of an intermediate drug-containing formulation.

The present invention provides a multi-layered tablet that possesses a triple combination release of active agents when placed in an environment of use.

The invention may be better understood by reference to the following definitions provided herein.

The term "intermediate drug-containing formulation" is employed herein to refer to a film-coated composition, an osmotic device, a coated tablet, a gastro-resistant coated core, a hard capsule, a gastro-resistant coated caplet, and other similar or equivalent dosage forms known to those of ordinary skill in the art.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "therapeutically effective amount" is the amount or quantity of drug, which is sufficient to elicit the required or desired therapeutic response, or in other words, the amount that is sufficient to elicit an appreciable biological response when administered to a patient.

By "immediate release" (IR) is meant a release of an active agent to an environment over a period of seconds to no more than about 30 minutes once release has begun and release begins within a second to no more than about 15 minutes after exposure to an aqueous environment. An immediate release composition, which does not possess a substantial delay in drug release, should be considered a subset of a rapid release composition. An immediate release composition releases drug in the buccal cavity, esophagus and/or stomach.

By "rapid release" (RR) is meant a release of an active agent to an environment over a period of seconds to no more than about 59 minutes once release has begun and release can begin within a few seconds or minutes after exposure to an aqueous environment or after expiration of a delay period (lag time) after exposure to an aqueous environment. In general, a rapid release composition releases drug releases drug in the stomach, jejunum or duodenum after oral administration, provided the composition does not include a delayed release material or delayed release coating. In such a case, the rapid release composition would release drug in the upper, middle and/or lower intestine or colon.

By "extended release" (ER) is meant a controlled release of an active agent from a dosage form to an environment over (throughout or during) an extended period of time, e.g. greater than or equal to one hour. As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. The term "extended release", as regards to drug release, includes the terms "controlled release", "prolonged release", "sustained release", or "slow release", as these terms are used in the pharmaceutical sciences.

By "controlled release" (CR) is meant a release of an active agent to an environment over a period of about eight hours up to about 12 hours, 16 hours, 18 hours, 20 hours, a day, or more than a day. A controlled release can begin within a few minutes after exposure to an aqueous environment or after expiration of a delay period (lag time) after exposure to an aqueous environment.

By "sustained release" (SR) is meant a controlled release of an active agent to maintain a constant drug level in the blood or target tissue of a subject to which the pharmaceutical composition is administered.

As used herein, a "dosage form" is a solid dosage form containing the pharmaceutical composition of the invention and being suitable for oral administration to a patient (subject).

A "zero-order" release profile characterizes the release profile of a dosage form that releases a constant amount of drug per unit time. A "pseudo-zero order" release profile is one that approximates a zero-order release profile.

A "first order" release profile characterizes the release profile of a dosage form that releases a constant percentage of an initial drug charge per unit time. A "pseudo-first order" release profile is one that approximates a first order release profile.

A "delayed but controlled or extended release dosage form" is one that provides a delayed release of a drug followed by a controlled or extended release of the drug. By "delayed release" (DR) is meant any formulation technique wherein release of the active substance from the dosage form is modified to occur at a later time than that from a conventional immediate release product. In other words, the beginning of the controlled release of drug is delayed by an initial period of time. The period of delay is generally about 5 minutes to 10 hours, or 30 minutes to 5 hours, or 1 hour to 3 hours.

As used herein, the term "release rate-controlling coating" refers to a coating surrounding a tablet that controls the rate of release of drug from an associated composition such that the drug is released substantially continuously over an extended period of time. A release rate-controlling coating is not a delayed release coating, since a delayed release coating does not control the rate of drug release. A delayed release coating merely delays the initial release of drug from an associated composition.

FIG. 1 depicts a multi-layered tablet (1) comprising two external drug-containing layers (3 and 4) in stacked arrangement with respect to and on opposite sides of an intermediate drug-containing formulation (2). The multi-layered tablet provides a triple combination release of at least one active agent. By "triple combination release" is meant that the multi-layered tablet provides three different drug release profiles for an active agent. In other words, each layer of the multi-layered tablet has its own drug release profile, or each of the three drug release profiles in a single multi-layered tablet is different than the other two. The rapid or immediate release layer (4) opposes and contacts the extended release layer (3). The intermediate drug-containing formulation is a controlled release dosage form in some embodiments.

Figure 2:
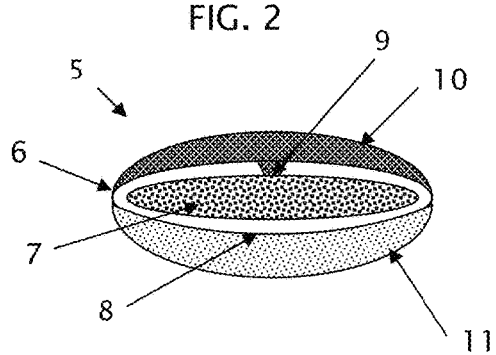
FIG. 2 depicts a cross-sectional view of a multi-layered tablet comprising two external drug-containing layers in stacked arrangement with respect to and on opposite sides of an osmotic device comprising a core coated with a semi-permeable membrane having a preformed passageway through it.

The intermediate drug-containing formulation can be an osmotic device. FIG. 2 depicts a multi-layered tablet (5) comprising two external drug-containing layers (10 and 11) in stacked arrangement with respect to and on opposite sides of an osmotic device (6) comprising a core (7) coated with a semipermeable membrane (8) having a preformed passageway (9) through it. In one embodiment, one of the external drug-containing layers (11) releases the drug in an immediate/rapid form, the other external drug-containing layer (10) releases the drug in an extended form, and the osmotic device releases the drug in a controlled form, as disclosed in Examples 1, 3, 4, 5 and 6. The preformed passageway can be adjacent the extended release layer or the immediate/rapid release layer. The preformed passageway can be made before or after the external drug-containing layers have been formed. The release of the drug from the osmotic core will begin after the external drug-containing layer no longer plugs the preformed passageway if the preformed passageway is made before the external drug-containing layers have been formed. The delayed period for initiation of the release will depend upon whether the preformed passageway is adjacent the immediate/rapid release layer or the extended release layer and upon whether or not the preformed passageway has been formed before or after attachment of the external layer(s).

Release of drug from the core of the osmotic device is delayed until the preformed passageway in the semipermeable membrane is uncovered or unplugged by any material superposing it. When the preformed passageway is adjacent the rapid or immediate release external layer but does not pass through the layer, and the osmotic device does not contain a delayed release composition, then release of drug from the core can begin shortly after the external layer has dissolved and/or eroded sufficiently to uncover the preformed passageway, e.g. 10, 20, or 30 minutes after placement of the device in an environment of use. When the preformed passageway is adjacent the extended release external layer but does not pass through the layer, and the osmotic device does not contain a delayed release composition, then release of drug from the core can be delayed and can begin shortly after the external layer has dissolved and/or eroded sufficiently to uncover the preformed passageway, e.g. at least 60 minutes after placement of the device in an environment of use. When the preformed passageway passes through an external layer superposing it, the release of drug from the core can begin shortly, e.g. minutes after placement of the device in an environment of use.

Figure 3:
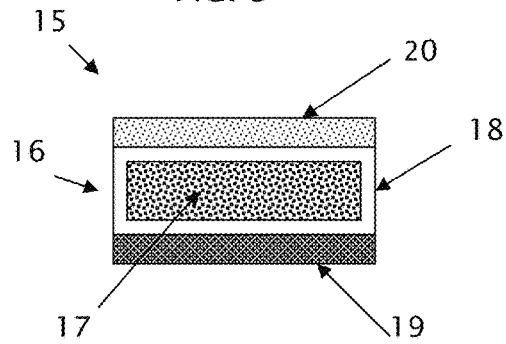
FIG. 3 depicts a cross-sectional view of a multi-layered tablet comprising two external drug-containing layers in stacked arrangement with respect to and on opposite sides of a gastro-resistant coated core.

FIG. 3 depicts a multi-layered tablet (15) comprising two external drug-containing layers (19 and 20) in stacked arrangement with respect to and on opposite sides of a gastro-resistant coated core (16). In one embodiment, one of the external drug-containing layers (20) releases the drug in an immediate/rapid form, the other external drug-containing layer (19) releases the drug in an extended form, and the gastro-resistant coated core (16) releases the drug in a delayed and extended form, as disclosed in Examples 2, 9 and 10, due to the gastro-resistant coating (18) surrounding the drug-containing core (17).

As used herein, a "gastro-resistant coated core" refers to a coated composition, wherein, after oral administration to a subject, the coating retains its integrity for a sufficient period of time to delay release of drug from the core until after the core has exited the gastric region. Materials suitable for use in making the coating of a gastro-resistant coated core are described herein.

Figure 4:
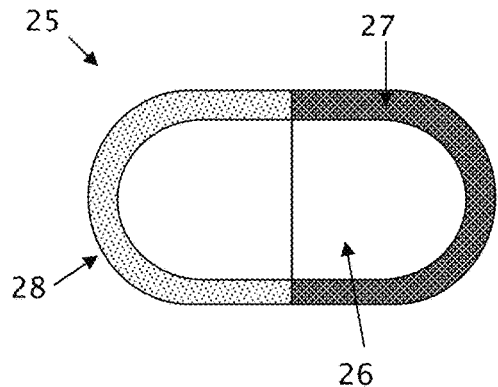
FIG. 4 depicts a partial cross-sectional view of a multi-layered tablet comprising two external drug-containing layers in stacked arrangement with respect to and on opposite sides of a hard capsule.

FIG. 4 depicts a multi-layered tablet (25) comprising two external drug-containing layers (27 and 28) in stacked arrangement with respect to and on opposite sides of a hard capsule (26). In one embodiment, one of the external drug-containing layers (28) releases the drug in an immediate/rapid form, the other external drug-containing layer (27) releases the drug in an extended form, and the hard capsule releases the drug in a controlled form, as disclosed in Example 8.

A capsule comprises a drug-containing composition enclosed within a capsule shell, which can be made of any material typically used for making such a shell. The term "shell" as used herein is taken to mean the shell of a capsule dosage form or the encasement or encapsulation material used to encapsulate fill compositions. Any material suitable for use in forming a capsule shell or in encapsulating another composition can be used according to the invention. An aqueous composition according to the invention is surrounded by a water (or aqueous medium) erodible, soluble, swellable and/or degradable shell or encapsulating material.

Materials suitable for the preparation of the capsule shell include by way of example and without limitation gelatin, hydroxypropyl methylcellulose, starch, animal gelatin, agar, fish (piscine) gelatin or a combination thereof. Other suitable materials include: polyvinyl alcohol/polyvinyl acetate copolymer (U.S. Pat. No. 3,300,546); a blend of hydroxybutyl methylcellulose and hydroxypropyl methylcellulose (U.S. Pat. No. 4,765,916); polyvinyl acetate (U.S. Pat. No. 2,560,649, U.S. Pat. No. 3,346,502); water-soluble gelatin (U.S. Pat. No. 3,525,426); polyvinyl alcohol (U.S. Pat. No. 3,528,921, U.S. Pat. No. 3,534,851, U.S. Pat. No. 3,556,765, U.S. Pat. No. 3,634,260, U.S. Pat. No. 3,671,439, U.S. Pat. No. 3,706,670, U.S. Pat. No. 3,857,195, U.S. Pat. No. 3,877,928, U.S. Pat. No. 4,367,156, U.S. Pat. No. 4,747,976, U.S. Pat. No. 5,270,054); polymers derived from such monomers as vinyl chloride, vinyl alcohol, vinyl pyrrolidone, furan, acrylonitrile, vinyl acetate, methyl acrylate, methyl methacrylate, styrene, vinyl ethyl ether, vinyl propyl ether, acrylamide, ethylene, propylene, acrylic acid, methacrylic acid, maleic anhydride, salts of any of the aforementioned acids and mixtures thereof; polyvinyl chloride; polypropylene; acrylic/maleic copolymers; sodium polyacrylate; polyvinyl pyrrolidone; glucomannan and optionally another natural polysaccharide with a polyhydric alcohol such as glycerin (U.S. Pat. No. 4,851,394); plastic and polylactide/polyglycolide (Elanco Animal Health Co.); HPMC (Shionogi Qualicaps Co. Ltd (Nara Japan); SUHEUNG CAPSULES CO. LTD. (KYUNGGI-DO, KOREA) and Capsugel); or a combination thereof. Essentially any material known to those of ordinary skill in the art as being for the preparation of capsule shell can be used in a capsule according to the invention. Suitable starch capsules can be made and used according to Vilivalam et al. (*Pharmaceutical Science & Technology Today* (2000), 3 (2), 64-69). A chitosan capsule for colonic delivery can be made and used according to Yamamoto (*Kobunshi* (1999), 48 (8), 595) or Tozaki et al. (*Drug Delivery System* (1997), 12 (5), 311-320).

The tableting machines useful to manufacture the multi-layered tablets of the invention have two powder filling positions and one internal core dispenser/centering device, such as for example the Fette machine model 4090, Kilian-Centra-Cota kind or Korsch-Central Core Coater 3C. These machines are able to take said cores, place and center them correctly into the die where the granulate is filled for the partial coating of said core. The dispenser can be adapted to dispense different dosage forms.

Some embodiments of the invention limit the intermediate drug-containing composition to a film-coated composition, e.g. an osmotic device, a capsule, a coated core, and the two external drug-containing layers, applied to the film-coated composition, to compressed layers. The film of the film-coated composition can be applied by spray-coating, such as for an osmotic device or a coated core, or it can be preformed, such as a capsule shell.

The present inventors have developed a process whereby a film-coated composition can be coated with two separated compressed compositions without rupturing the film of the film-coated composition during the compression steps. Thus, a multi-layered tablet is prepared by a process comprising:

providing a drug-containing rapid release or extended release composition and compressing said composition in a die with a convex punch to form a compressed concave composition;

providing a preformed intermediate drug-containing composition and placing it on the compressed concave composition in the die;

placing a drug-containing extended release or rapid release composition, respectively, over the intermediate drug-containing composition and compressing it with a punch, thereby forming the multi-layered tablet.

The compression surface of the punch can be flat, convex, concave or a combination thereof. When a flat compression surface is used, the resulting compressed composition will have a flat mating surface. When a convex compression surface is used, the resulting compressed composition will have a concave mating surface. When a concave compression surface is used, the resulting compressed composition will have a convex mating surface. The multi-layered tablet of FIG. 3 is made using a flat punch. The multi-layered tablet of FIG. 2 is made using a convex punch. The multi-layered tablets of FIGS. 1 and 4 is made using a punch having a combination flat and convex surface.

By virtue of the process employed in making the multi-layered tablet, the external layers are not concentric. Instead, they are in stacked arrangement with respect to each other and the intermediate drug-containing composition, and they oppose each other, meaning they are located on opposite sides, ends or faces of the intermediate drug-containing composition. The external compressed layers may (FIGS. 1, 4) or may not (2, 3) contact each other. The invention also includes embodiments that are combinations of the multi-layered tablets depicted in FIGS. 1-4.

The pharmaceutical compositions comprise in the multi-layered tablet of the invention can include a wide range of different excipients. Suitable types of excipients include adsorbents, antioxidants, acidifying agent, alkalizing agent, buffering agents, colorants, flavorants, sweetening agents, tablet antiadherents, tablet binders, tablet diluents, tablet direct compression excipients, tablet disintegrants, tablet glidants, tablet lubricants, tablet opaquants and/or tablet polishing agents. Similar excipients used in capsule formulations can also be include in the multi-layered tablet of the invention.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium for product stability. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "antiadherent" is intended to mean an agent that prevents the sticking of tablet formulation ingredients to punches and dies in a tableting machine during production. Such compounds include, by way of example and without limitation, magnesium stearate, talc, calcium stearate, glyceryl behenate, polyethylene glycol (PEG), hydrogenated vegetable oil, mineral oil, stearic acid and other materials known to one of ordinary skill in the art.

As used herein, the term "binder" is intended to mean a substance used to cause adhesion of powder particles in granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC™ F68, PLURONIC™ F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "glidant" is intended to mean an agent used in tablet and capsule formulations to promote flowability of the granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "lubricant" is intended to mean a substance used in the instant formulations to reduce friction during compression or other processing. Such compounds include, by way of example and without limitation, calcium stearate, magnesium stearate, mineral oil, stearic acid, and zinc stearate and other materials known to one of ordinary skill in the art.

As used herein, the term "opaquant" is intended to mean a compound used to render a capsule or a tablet coating opaque. May be used alone or in combination with a colorant. Such compounds include, by way of example and without limitation, titanium dioxide, talc and other materials known to one of ordinary skill in the art.

As used herein, the term "polishing agent" is intended to mean a compound used to impart an attractive sheen to coated tablets. Such compounds include, by way of example and without limitation, carnauba wax, white wax and other materials known to one of ordinary skill in the art.

As used herein, the term "disintegrant" is intended to mean a compound used in solid dosage forms to promote the disruption of the solid mass into smaller particles that are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth; crospovidone and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors that have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particular flavors are the grape and cherry flavors and citrus flavors such as orange.

The present multi-layered tablet can also employ one or more commonly known surface-active agents or cosolvents that improve wetting or disintegration of the tablet core or layers.

Plasticizers can also be included in the multi-layered tablet of the invention to modify the properties and characteristics of the polymers used in the coats or core of the tablet. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

The multi-layered tablet of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

Various other components, not otherwise listed above, can be added to the multi-layered tablet of the invention for optimization of a desired active agent release profile including, by way of example and without limitation, glycerylmonostearate, nylon, cellulose acetate butyrate, d,l-poly (lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly(vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

The dosage forms of the invention can include surface markings, cuttings, grooves, letters and/or numerals for the purposes of decoration, identification and/or other purposes.

The multi-layered tablet can include a finish coat as is commonly done in the art to provide the desired shine, color, taste or other aesthetic characteristics. Materials suitable for preparing the finish coat are well known in the art and found in the disclosures of many of the references cited and incorporated by reference herein.

Materials which are suitable for use in an immediate release or rapid release coating include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble and low molecular weight cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; croscarmellose sodium; other cellulose polymers such as sodium carboxymethylcellulose; and other materials known to those of ordinary skill in the art. Other materials include poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer. The artisan of ordinary skill will recognize that the above-noted materials include film-forming polymers that are not release rate controlling materials even though they may include the same chemical functionality thereof. This is because film-forming polymers that do not control release rate generally have lower molecular weight than otherwise similar film-forming polymers having higher molecular weight.

The immediate release or rapid release coating can also include a water soluble and/or erodible, inert and non-toxic material that is at least partially, and optionally substantially completely, soluble or erodible in an environment of use. Exemplary materials are disclosed in U.S. Pat. No. 4,576,604 to Guittard et al. and U.S. Pat. No. 4,673,405 to Guittard et al., and U.S. Pat. No. 6,004,582 to Faour et al. and the text *Pharmaceutical Dosage Forms: Tablets Volume I*, $2^{nd}$ Edition. (A. Lieberman. ed. 1989, Marcel Dekker, Inc.), the relevant disclosures of which are hereby incorporated by reference.

A "gastro-resistant coating" or delayed release material (coating) used in the multi-layered tablet of the invention will possess limited solubility or erodibility or be insoluble or non-erodible in a first external fluid, while being soluble and/or erodible in a second external fluid. For example, the delayed release material may be insoluble in the fluid of a first environment of use, such as gastric juices, acidic fluids, or polar liquids, and soluble or erodible in the fluid of a second environment of use, such as intestinal juices, substantially pH neutral or basic fluids, or apolar liquids. A wide variety of other polymeric materials are known to possess these various solubility properties and can be used. Such other polymeric materials include, by way of example and without limitation, cellulose acetate phthalate (CAP), cellulose acetate trimelletate (CAT), poly(vinyl acetate)phthalate (PVAP), hydroxypropyl methylcellulose phthalate (HP-MCP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, EUDRAGIT™ L-30-D (MA-EA, 1:1), EUDRAGIT™ L-100-55 (MA-EA, 1:1), hydroxypropyl methylcellulose acetate succinate (HPMCAS), COATERIC™ (PVAP), AQUATERIC™ (CAP), AQOAT™ (HP-MCAS) and combinations thereof.

An optional polymeric material for the delayed release material/coating is a poly(vinylpyrrolidone)-vinyl acetate copolymer, such as the material supplied by BASF under its KOLLIDON VA64 trademark. This can be mixed with other excipients such as magnesium stearate, povidone, which is supplied by BASF under its KOLLIDON K 30 trademark, and hydroxypropyl methylcellulose, which is supplied by Dow under its METHOCEL E-15 trademark. The materials can be prepared in solutions having different concentrations of polymer according to the desired solution viscosity. For example, a 10% P/V aqueous solution of KOLLIDON™ K 30 has a viscosity of about 5.5-8.5 cps at 20° C., and a 2% P/V aqueous solution of METHOCEL™ E-15 has a viscosity of about 13-18 cps at 20° C.

The delayed release composition can also comprise other materials suitable which are substantially resistant to gastric juices and which will promote enteric release. These materials do not dissolve, disintegrate, or change their structure in the stomach and during the period of time that the dosage form resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate (such as SURETERIC™ of Colorcon), diethyl phthalate, dibutyl phthalate, dialkyl phthalate wherein the alkyl comprises from 1 to 7 straight and branched alkyl groups, aryl phthalates, and other materials known to one or ordinary skill in the art.

By "release rate-controlling material" or "release rate modifier" is meant a compound or combination of compounds that regulate or control the release of active agent from an extended release composition or layer. The release rate-controlling material can be included within the matrix of an extended release composition and/or it can be included in a film (coating) surrounding an extended release composition. For example, an extended release composition or layer can comprise a release rate-controlling film and/or an embedded release rate-controlling material within its matrix. The release rate-controlling material will assist in providing an extended release of the therapeutic agent and can cooperate with other components in the formulation to provide either a delayed, sustained, timed, pH dependent, targeted, or further controlled delivery of the therapeutic agent. It will be understood that some of the binders mentioned herein can also be considered release rate modifiers. Exemplary compounds suitable for use as a release rate-controlling material include, without limitation, HPMC (hydroxypropyl methylcellulose), HPC (hydroxypropylcellulose), PEO (poly(ethylene oxide)), cellulose acetate butyrate, cellulose acetate propionate, cellulose propionate, carrageenan, cellulose acetate, cellulose nitrate, methylcellulose, hydroxyethyl cellulose, ethylcellulose, polyvinyl acetate, latex dispersions, acacia, tragacanth, guar gum, gelatin, wax, and combinations thereof.

Other suitable polymers are well-known excipients commonly used in the field of pharmaceutical formulations and are included in, for example, *Remington's Pharmaceutical Sciences,* 18*th Edition*, Alfonso R. Gennaro (editor), Mack Publishing Company, Easton, Pa., 1990, pp. 291-294; Alfred Martin, James Swarbrick and Arthur Commarata, *Physical Pharmacy. Physical Chemical Principles in Pharmaceutical Sciences,* 3*rd edition* (Lea & Febinger, Philadelphia, Pa., 1983, pp. 592-638); A. T. Florence and D. Altwood, (*Physicochemical Principles of Pharmacy, 2nd Edition,* MacMillan Press, London, 1988, pp. 281-334. The entire disclosures of the references cited herein are hereby incorporated by references. Still other suitable polymers include water-soluble natural polymers, water-soluble semisynthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

Solutes can be added to the tablet. These solutes can aid in either the suspension or dissolution of drug. Exemplary solutes include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art.

In standard dissolution assays, the values can vary depending upon the conditions employed. Moreover, the values may have an absolute standard deviation (STD) of ±10%, ±5% or ±3% at each given time point.

Amantadine can be administered to late-stage Parkinsonian patients as adjunct (add-on or combination) therapy to levodopa for treating dyskinesias. For example, PCT International Publication No. WO04/087116 to Vergez et al.

discloses a phase II, controlled study in a double-blind setting carried out to evaluate the impact of the combination of amantadine and citalopram in the UPDRS score of patients suffering from motor fluctuations. The study showed clear evidences that amantadine on top of levodopa treatment produced a significant improvement in all of the motor fluctuation-related scores (UPDRS and AIMS) in fluctuating patients.

Example 1 discloses an exemplary multi-layered tablet comprising an osmotic core that provides amantadine ER, and an external IR or RR levodopa/carbidopa-containing layer and an external ER levodopa-containing layer in stacked arrangement with respect to and on opposite sides of the osmotic core.

Figure 5:
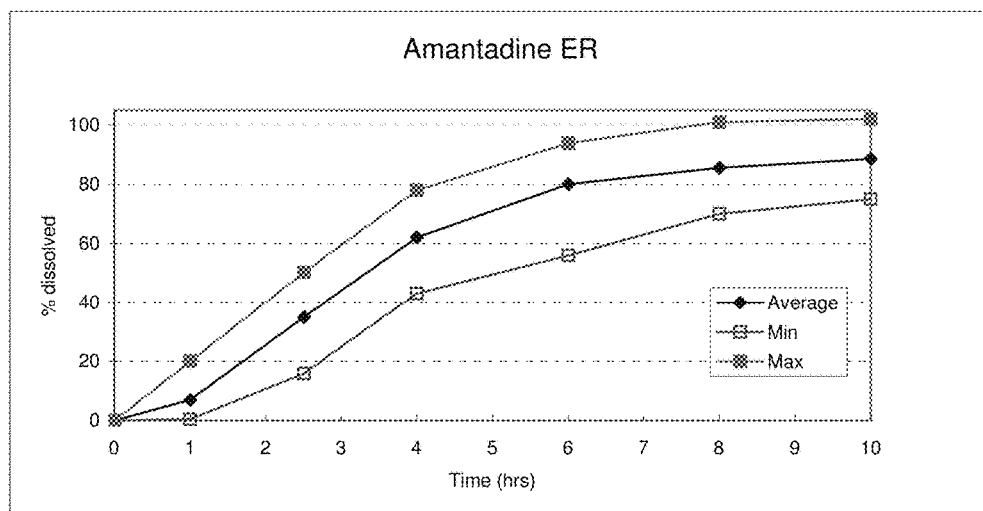
FIG. 5 depicts the in vitro release profile of amantadine from the exemplary multi-layered tablet of Example 1.
Figure 6:
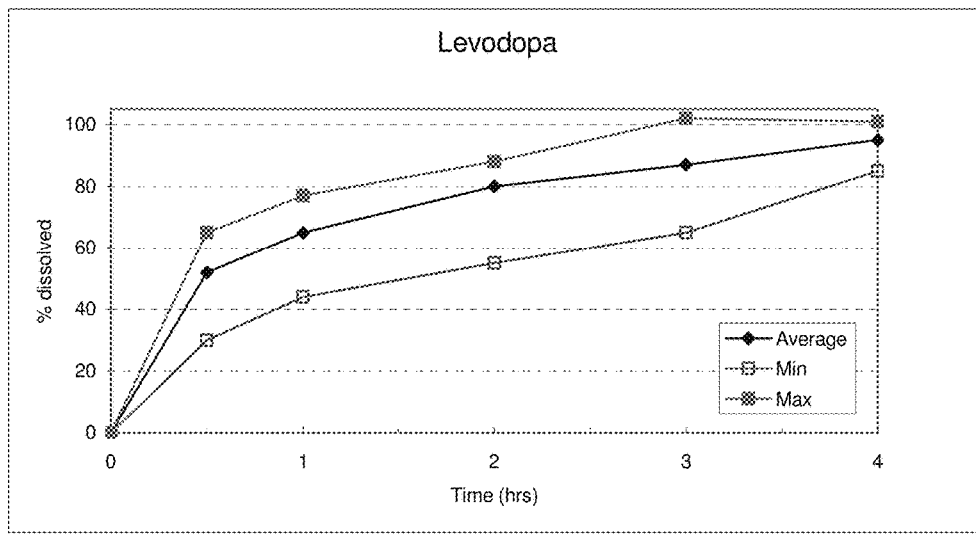
FIG. 6 depicts the in vitro release profile of levodopa from the exemplary multi-layered tablet of Example 1.
Figure 7:
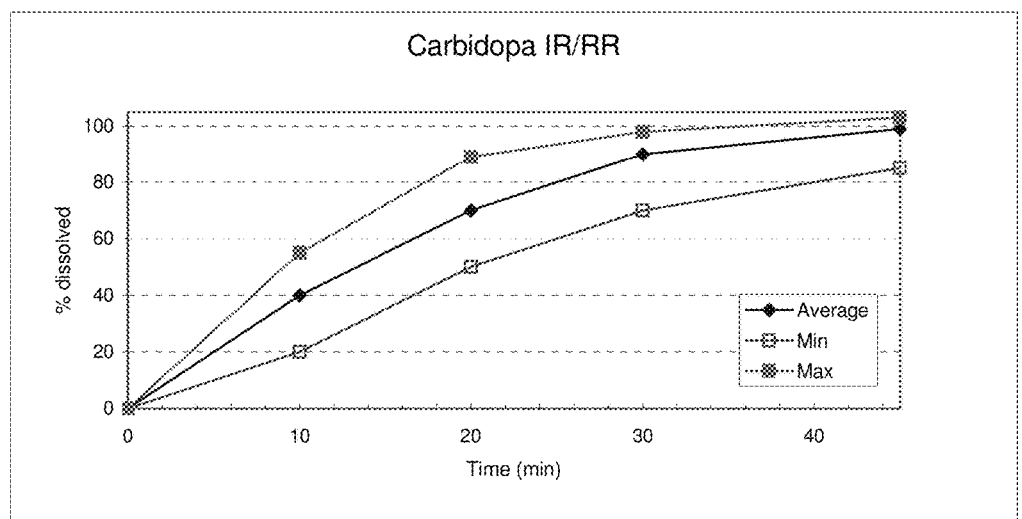
FIG. 7 depicts the in vitro release profile of carbidopa from the exemplary multi-layered tablet of Example 1.

FIGS. 5, 6, and 7 depict the release profile for formulations prepared as disclosed in Example 1. The in vitro testing was performed with USP Type II dissolution apparatus (paddles), in 900 ml of HCl 0.1N maintained at a temperature of 37±0.5° C. The samples were tested by high pressure liquid chromatography. The amantadine release profile of the multi-layered tablets of Example 1 is described as follows and disclosed in FIG. 5. The time is measured as from the instant that the tablet is initially placed in an aqueous environment.

| Time (hrs) | Average Released (%) | SD | Min | Max |
| --- | --- | --- | --- | --- |
| 0 | 0 | 0 | 0 | 0 |
| 1 | 7 | 7.5 | 0 | 20 |
| 2.5 | 35 | 9.0 | 16 | 50 |
| 4 | 62 | 10.2 | 43 | 78 |
| 6 | 80 | 8.2 | 56 | 94 |
| 8 | 86 | 5.6 | 70 | 101 |
| 10 | 89 | 4.2 | 75 | 102 |

The levodopa release profile of the multi-layered tablets of Example 1 is disclosed in FIG. 6 and described as follows. The time is measured as from the instant that the tablet is initially placed in an aqueous environment.

| Time (hrs) | Average | SD | Min | Max |
| --- | --- | --- | --- | --- |
| 0 | 0 | 0 | 0 | 0 |
| 0.5 | 52 | 10.0 | 30 | 65 |
| 1 | 65 | 6.0 | 44 | 77 |
| 2 | 80 | 4.0 | 55 | 88 |
| 3 | 87 | 5.5 | 65 | 102 |
| 4 | 95 | 3.5 | 85 | 101 |

The carbidopa release profile of the multi-layered tablets of Example 1 is disclosed in FIG. 7 and described as follows. The time is measured as from the instant that the tablet is initially placed in an aqueous environment.

| Time (min) | Average Released (%) | SD | Min | Max |
| --- | --- | --- | --- | --- |
| 0 | 0 | 0 | 0 | 0 |
| 10 | 40 | 5.9 | 20 | 55 |
| 20 | 70 | 7.4 | 50 | 89 |
| 30 | 90 | 6.6 | 70 | 98 |
| 45 | 99 | 4.8 | 85 | 103 |

Example 2 discloses an exemplary multi-layered tablet comprising a gastro-resistant coated core that provides a delayed and extended release of levodopa, and an external IR or RR levodopa/carbidopa-containing layer and an external ER amantadine-containing layer in stacked arrangement with respect to and on opposite sides of the gastro-resistant coated core.

Figure 8:
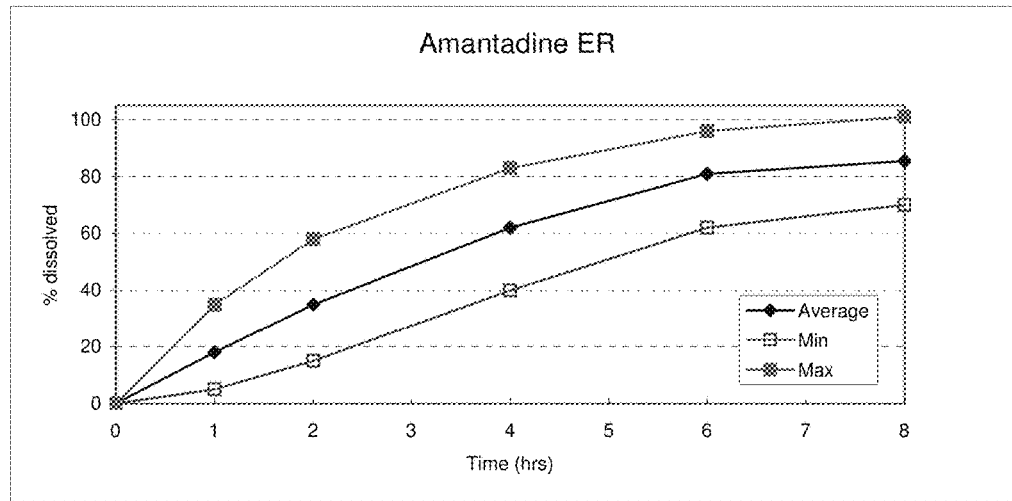
FIG. 8 depicts the in vitro release profile of amantadine from the exemplary multi-layered tablet of Example 2.
Figure 9:
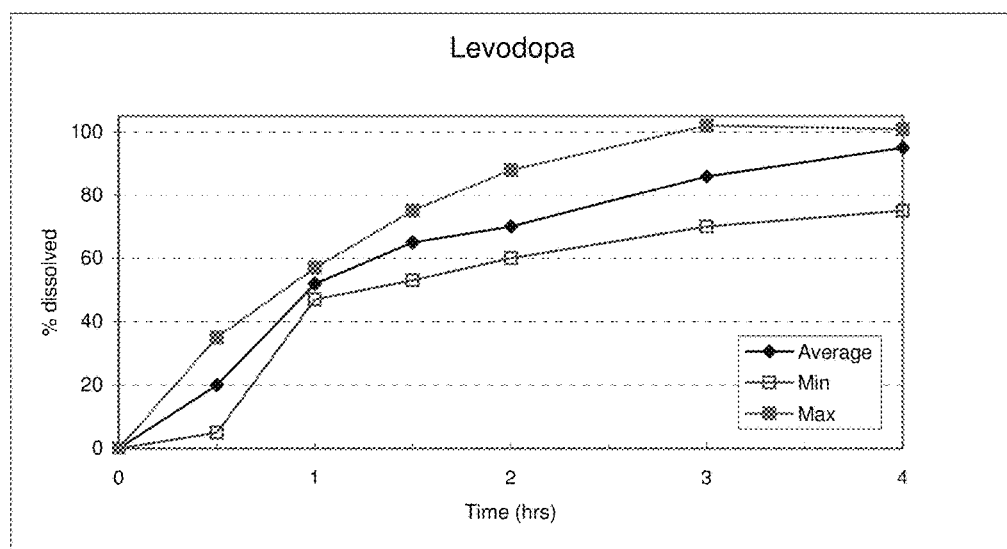
FIG. 9 depicts the in vitro release profile of levodopa from the exemplary multi-layered tablet of Example 2.
Figure 10:
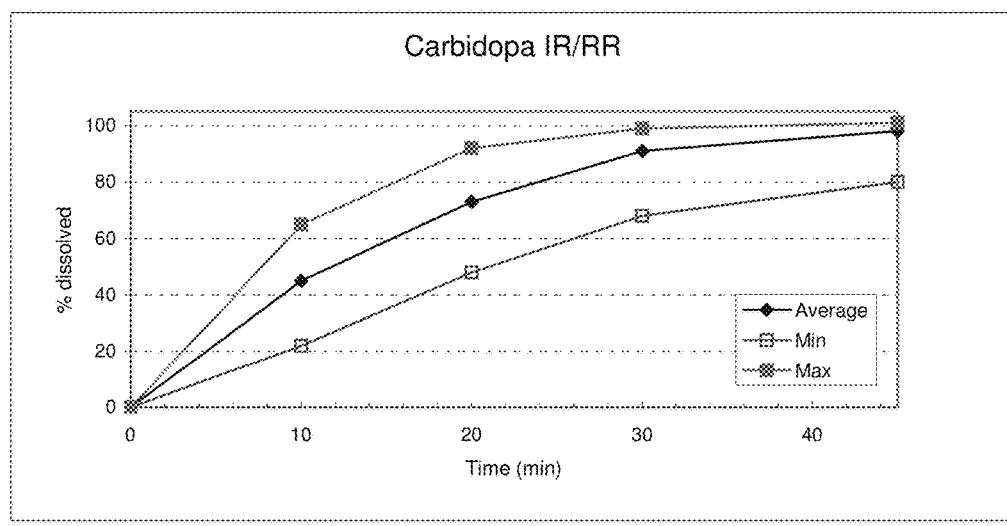
FIG. 10 depicts the in vitro release profile of carbidopa from the exemplary multi-layered tablet of Example 2.

FIGS. 8, 9, and 10 depict the release profile for formulations prepared as disclosed in Example 2. The in vitro testing is performed with USP Type II dissolution apparatus (paddles), first in 700 ml of HCl 0.1N maintained at a temperature of 37±0.5° C., during 1 hour, and then in 900 ml phosphate buffer pH 6 with 0.5-1% tween 80 or sodium lauryl sulfate. The samples were tested by high pressure liquid chromatography. The amantadine release profile of the multi-layered tablets of Example 2 is described as follows and disclosed in FIG. 8. The time is measured as from the instant that the tablet is initially placed in an aqueous environment.

| Time (hrs) | Average Released (%) | SD | Min | Max |
| --- | --- | --- | --- | --- |
| 0 | 0 | 0 | 0 | 0 |
| 1 | 18 | 6.3 | 5 | 35 |
| 2 | 35 | 5.7 | 15 | 58 |
| 4 | 62 | 4.7 | 40 | 83 |
| 6 | 81 | 6.2 | 62 | 96 |
| 8 | 86 | 7.3 | 70 | 101 |

The levodopa release profile of the multi-layered tablets of Example 2 is described as follows and disclosed in FIG. 9. The time is measured as from the instant that the tablet is initially placed in an aqueous environment.

| Time (hrs) | Average Released (%) | SD | Min | Max |
| --- | --- | --- | --- | --- |
| 0 | 0 | 0 | 0 | 0 |
| 0.5 | 20 | 5.6 | 5 | 35 |
| 1 | 52 | 7.3 | 47 | 57 |
| 1.5 | 65 | 6.4 | 53 | 75 |
| 2 | 70 | 7.2 | 60 | 88 |
| 3 | 86 | 7.5 | 70 | 102 |
| 4 | 95 | 4.6 | 75 | 101 |

The carbidopa release profile of the multi-layered tablets of Example 2 is described as follows and disclosed in FIG. 10. The time is measured as from the instant that the tablet is initially placed in an aqueous environment.

| Time (min) | Average Released (%) | SD | Min | Max |
| --- | --- | --- | --- | --- |
| 0 | 0 | 0 | 0 | 0 |
| 10 | 45 | 4.9 | 22 | 65 |
| 20 | 73 | 6.8 | 48 | 92 |
| 30 | 91 | 8.7 | 68 | 99 |
| 45 | 98 | 5.4 | 80 | 101 |

Example 7 discloses an exemplary multi-layered tablet comprising a matrix core that provides amantadine ER, and an external IR or RR levodopa/carbidopa-containing layer and an external ER levodopa-containing layer in stacked arrangement with respect to and on opposite sides of the matrix core.

Figure 11:
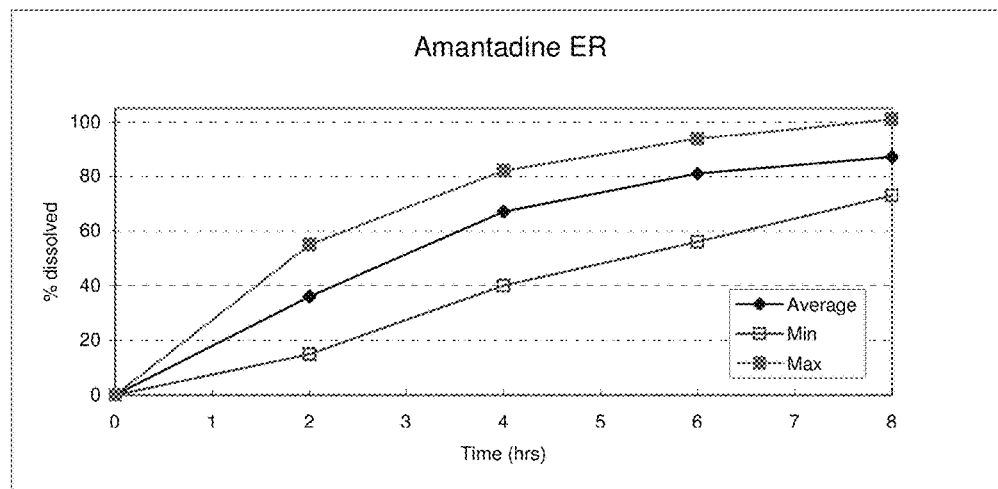
FIG. 11 depicts the in vitro release profile of amantadine from the exemplary multi-layered tablet of Example 7.
Figure 12:
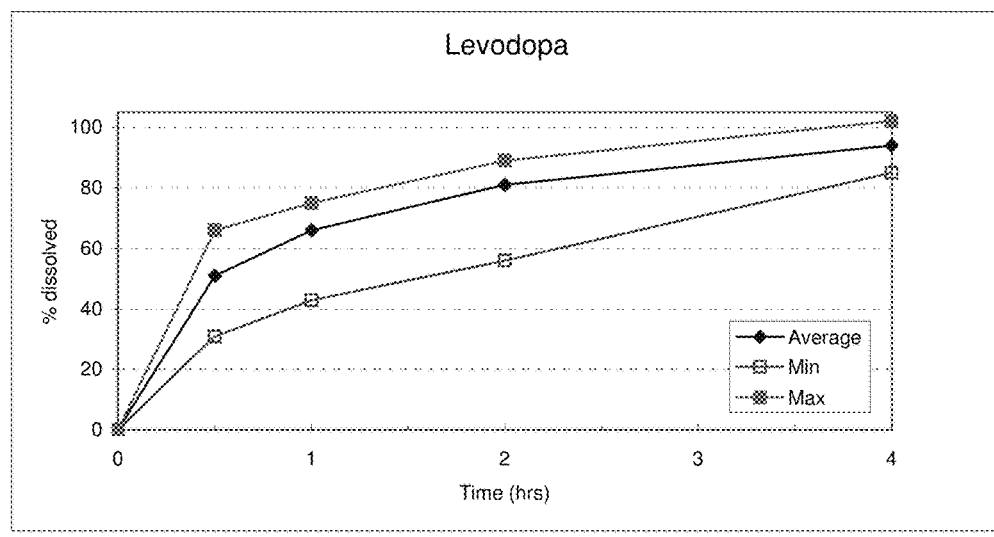
FIG. 12 depicts the in vitro release profile of levodopa from the exemplary multi-layered tablet of Example 7.
Figure 13:
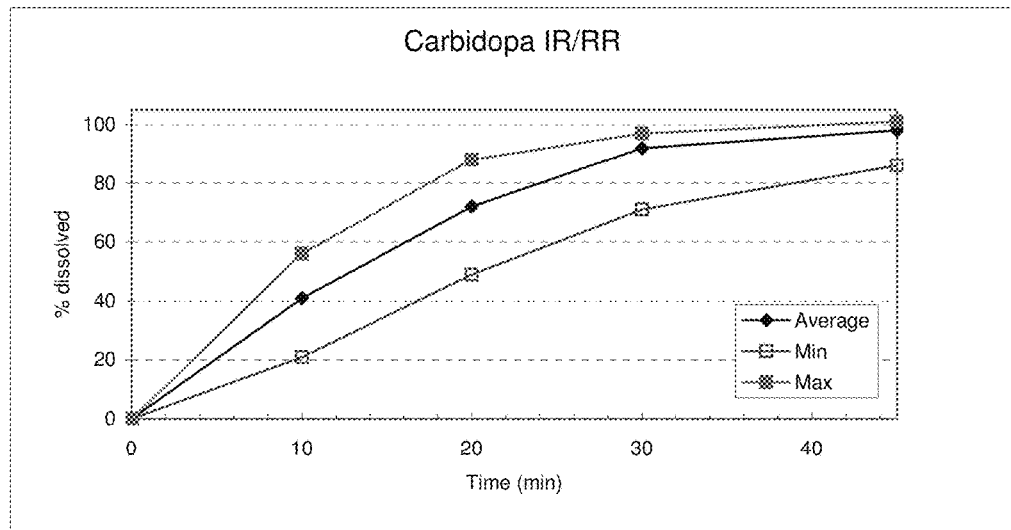
FIG. 13 depicts the in vitro release profile of carbidopa from the exemplary multi-layered tablet of Example 7.

FIGS. 11, 12, and 13, depict the release profile for formulations prepared as disclosed in Example 7. The in vitro testing is performed with USP Type II dissolution apparatus (paddles), in 900 ml of HCl 0.1N at 50 rpm maintained at a temperature of 37±0.5° C. The amantadine release profile of the multi-layered tablets of Example 7 is disclosed in FIG. 11 and described as follows. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 2 | 36 | 5.0 | 15 | 55 |
| 4 | 67 | 4.6 | 40 | 82 |
| 6 | 81 | 2.3 | 56 | 94 |
| 8 | 87 | 4.7 | 73 | 101 |

The levodopa release profile of the multi-layered tablets of Example 7 is disclosed in FIG. 12 and described as follows. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 0.5 | 51 | 12.5 | 31 | 66 |
| 1 | 66 | 7.9 | 43 | 75 |
| 2 | 81 | 6.6 | 56 | 89 |
| 4 | 94 | 6.4 | 85 | 102 |

The carbidopa release profile of the multi-layered tablets of Example 7 is disclosed in FIG. 13 and described as follows. The time is measured as from the instant that the tablet is initially placed in an aqueous environment.

| Time (min) | Average Released (%) | SD | Min | Max |
|---|---|---|---|---|
| 0 | 0 | 0 | 0 | 0 |
| 10 | 41 | 6.4 | 21 | 56 |
| 20 | 72 | 8.5 | 49 | 88 |
| 30 | 92 | 7.4 | 71 | 97 |
| 45 | 98 | 7.1 | 86 | 101 |

The medications with the most evidence of efficacy in generalized anxiety disorder (GAD) are the benzodiazepines, including a new long-acting formulation of alprazolam. These drugs have a low incidence of side effects but may cause physical dependence, withdrawal, and sedation. Antidepressants are also efficacious in GAD but act less quickly than benzodiazepines (Rickels et al, J Clin Psychiatry. 2002; 63 Suppl 14:9-16). Combining venlafaxine and alprazolam may lead to an increase in improvement in patients not responding to one treatment approach alone; and adding ondansetron to the combination may help to avoid discontinuation of treatment do to nausea commonly caused by venlafaxine.

Example 3 discloses a multi-layered tablet comprising an osmotic core that provides venlafaxine CR, and an external IR or RR ondansetron-containing layer and an external ER alprazolam-containing layer in stacked arrangement with respect to and on opposite sides of the osmotic core.

Figure 14:
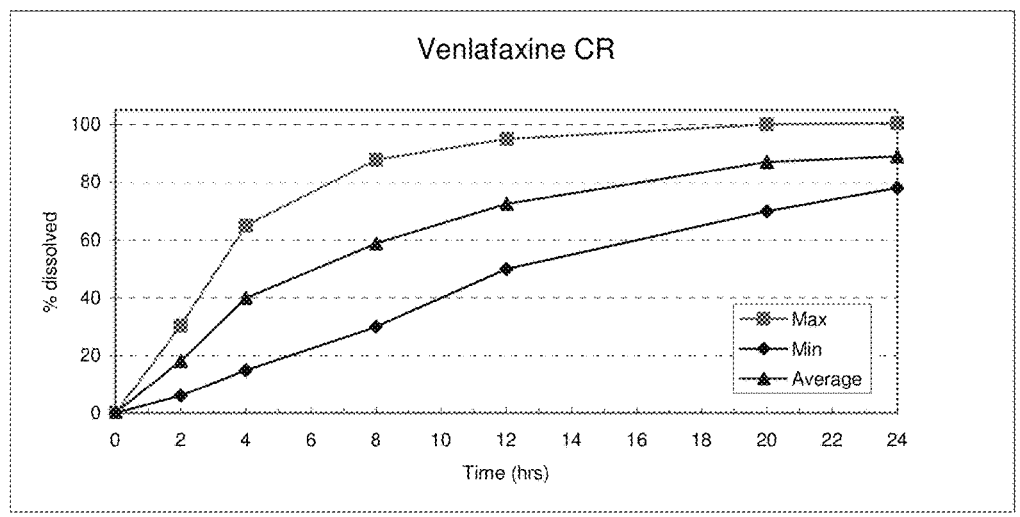
FIG. 14 depicts the in vitro release profile of venlafaxine from the exemplary multi-layered tablet of Example 3.
Figure 15:
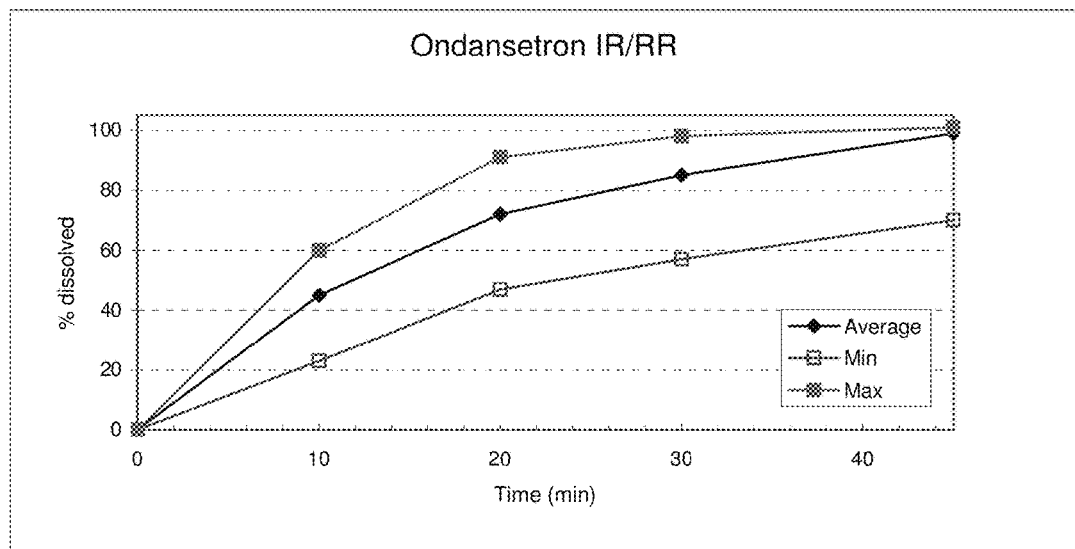
FIG. 15 depicts the in vitro release profile of ondansetron from the exemplary multi-layered tablet of Example 3.
Figure 16:
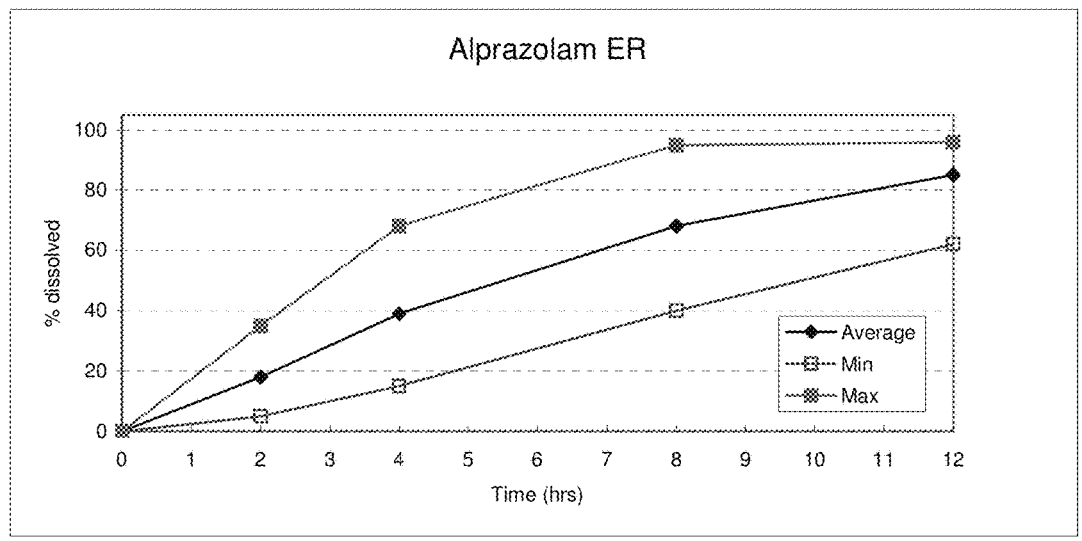
FIG. 16 depicts the in vitro release profile of alprazolam from the exemplary multi-layered tablet of Example 3.

FIGS. 14, 15, and 16 depict the release profile for formulations prepared as disclosed in Example 3. The in vitro testing is performed with USP Type II dissolution apparatus (paddles), in 900 ml of HCl 0.1N with 0.1% tween, maintained at a temperature of 37±0.5° C. The venlafaxine release profile of the multi-layered tablets of Example 3 is disclosed in FIG. 14 and described as follows. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 2 | 18 | 15.9 | 6 | 30 |
| 4 | 40 | 8.6 | 15 | 65 |
| 8 | 59 | 11.5 | 30 | 88 |
| 12 | 73 | 4.9 | 50 | 95 |
| 20 | 87 | 6.5 | 70 | 100 |
| 24 | 89 | 6.4 | 78 | 101 |

The ondansetron release profile of the multi-layered tablets of Example 3 is disclosed in FIG. 15 and described as follows. The time is measured as from the instant that the tablet is initially placed in an aqueous environment.

| Time (min) | Average Released (%) | SD | Min | Max |
|---|---|---|---|---|
| 0 | 0 | 0 | 0 | 0 |
| 10 | 45 | 4.9 | 23 | 60 |
| 20 | 72 | 6.8 | 47 | 91 |
| 30 | 85 | 8.7 | 57 | 98 |
| 45 | 99 | 5.4 | 70 | 101 |

The alprazolam release profile of the multi-layered tablets of Example 3 is disclosed in FIG. 16 and described as follows. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 2 | 18 | 6.3 | 5 | 35 |
| 4 | 39 | 5.7 | 15 | 68 |
| 8 | 68 | 4.7 | 40 | 95 |
| 12 | 85 | 6.2 | 62 | 96 |

Example 8 discloses a multi-layered tablet comprising a capsule containing venlafaxine CR micro-osmotic tablets, and an external IR or RR ondansetron-containing layer and an external ER alprazolam-containing layer in stacked arrangement with respect to and on opposite sides of the capsule.

Figure 17:
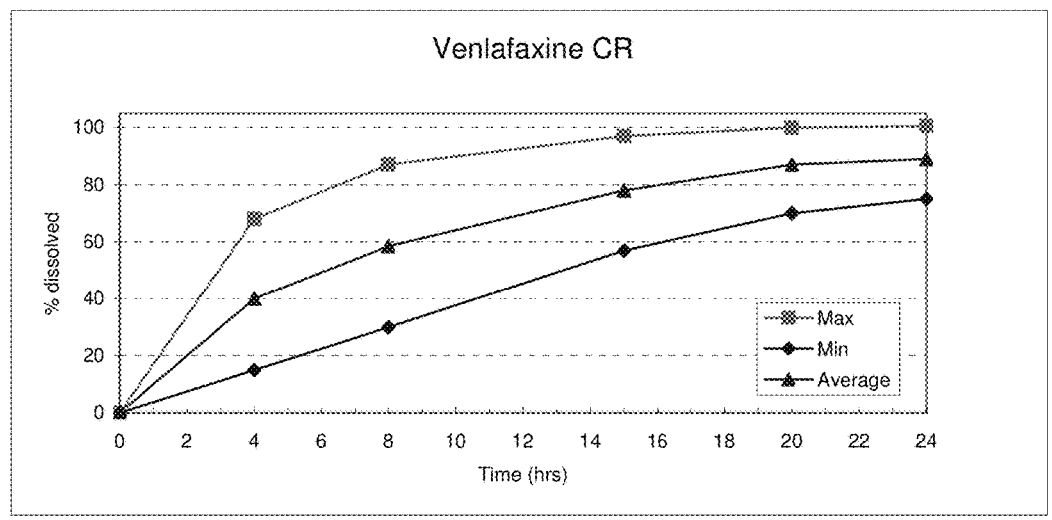
FIG. 17 depicts the in vitro release profile of venlafaxine from the exemplary multi-layered tablet of Example 8.
Figure 18:
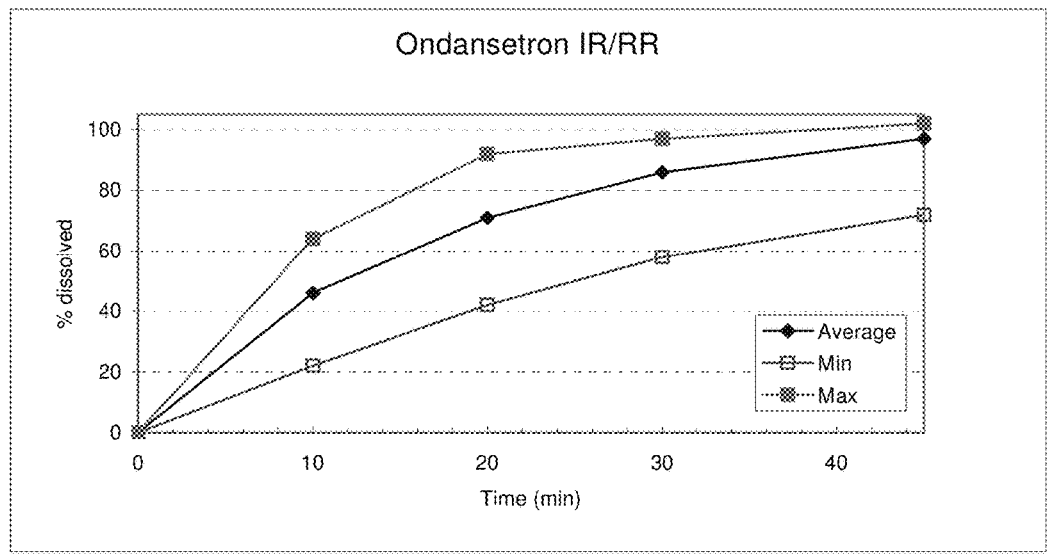
FIG. 18 depicts the in vitro release profile of ondansetron from the exemplary multi-layered tablet of Example 8.
Figure 19:
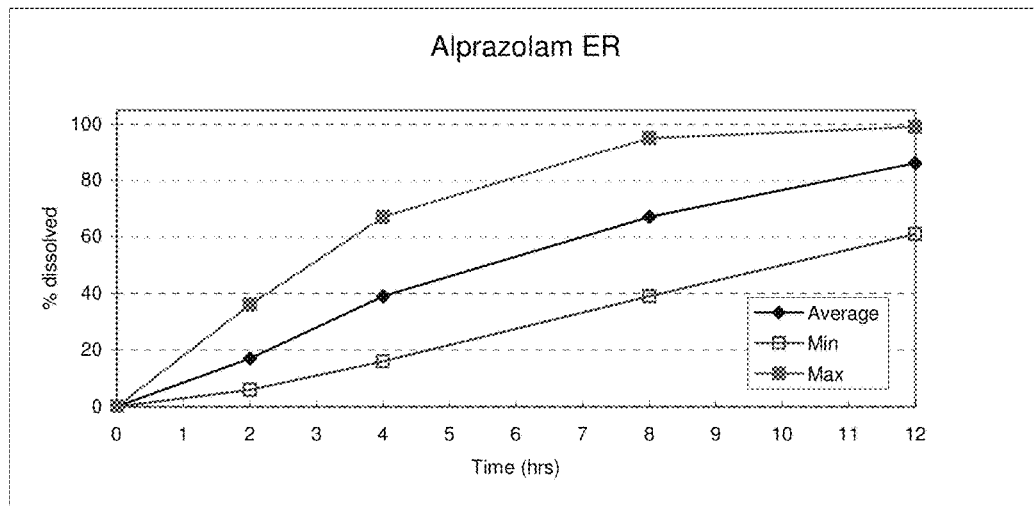
FIG. 19 depicts the in vitro release profile of alprazolam from the exemplary multi-layered tablet of Example 8.

FIGS. 17, 18, and 19 depict the release profile for formulations prepared as disclosed in Example 8. The in vitro testing is performed with USP Type II dissolution apparatus (paddles), in 900 ml of HCl 0.1N with 0.1% tween at 50 rpm maintained at a temperature of 37±0.5° C. The venlafaxine release profile of the multi-layered tablets of Example 8 is disclosed in FIG. 17 and described as follows. The time is measured as from the instant that the tablet is initially placed in an aqueous environment.

| Time (hrs) | Average Released (%) | SD | Min | Max |
| --- | --- | --- | --- | --- |
| 0 | 0 | 0 | 0 | 0 |
| 4 | 40 | 8.7 | 15 | 68 |
| 8 | 59 | 11.5 | 30 | 87 |
| 15 | 78 | 10.4 | 57 | 97 |
| 20 | 87 | 8.9 | 70 | 100 |
| 24 | 89 | 7.8 | 75 | 101 |

The ondansetron release profile of the multi-layered tablets of Example 8 is disclosed in FIG. 18 and described as follows. The time is measured as from the instant that the tablet is initially placed in an aqueous environment.

| Time (min) | Average Released (%) | SD | Min | Max |
| --- | --- | --- | --- | --- |
| 0 | 0 | 0 | 0 | 0 |
| 10 | 46 | 5.6 | 22 | 64 |
| 20 | 71 | 6.7 | 42 | 92 |
| 30 | 86 | 8.4 | 58 | 97 |
| 45 | 97 | 5.1 | 72 | 102 |

The alprazolam release profile of the multi-layered tablets of Example 8 is disclosed in FIG. 19 and described as follows. The time is measured as from the instant that the tablet is initially placed in an aqueous environment.

| Time (hrs) | Average Released (%) | SD | Min | Max |
| --- | --- | --- | --- | --- |
| 0 | 0 | 0 | 0 | 0 |
| 2 | 17 | 5.8 | 6 | 36 |
| 4 | 39 | 6.7 | 16 | 67 |
| 8 | 67 | 6.4 | 39 | 95 |
| 12 | 86 | 2.3 | 61 | 99 |

Coadministration of levodopa and carbidopa can be used for treating Parkinson's disease. Examples of additional active agents that may function to augment or improve the treatment or conditions associated with Parkinson's disease include selegiline, COMT inhibitors such as entacapone or tolcapone, and dopamine agonists such as bromocriptine, ropinirole, pergolide, rotigotine, or pramipexole, and stomach motility modulators such as mosapride or domperidone. These active agents can be used alone or in combinations of two, three, four or more active agents.

Example 4 discloses a multi-layered tablet comprising an osmotic core that provides ropinirole CR, and an external IR or RR levodopa/carbidopa-containing layer and an external ER levodopa-containing layer in stacked arrangement with respect to and on opposite sides of the osmotic core.

Figure 20:
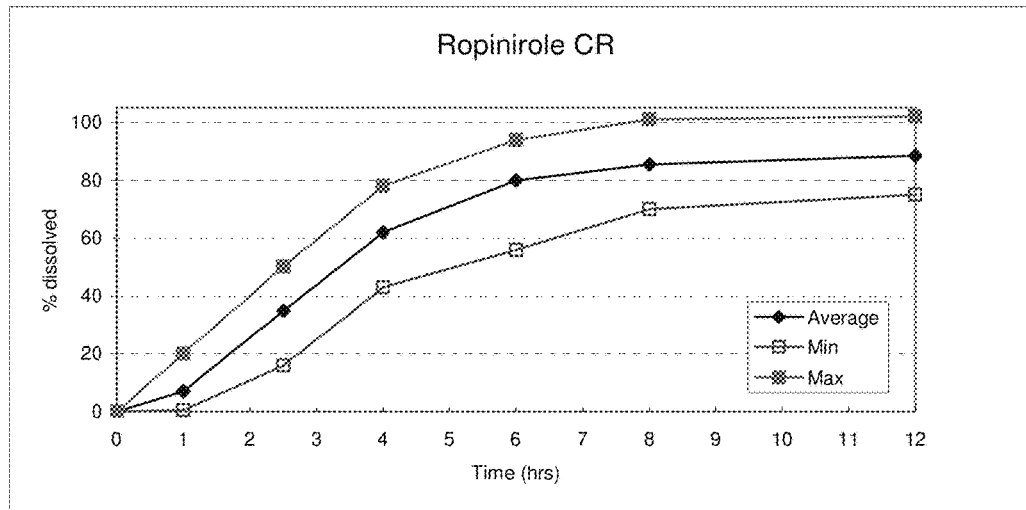
FIG. 20 depicts the in vitro release profile of ropinirole from the exemplary multi-layered tablet of Example 4.
Figure 21:
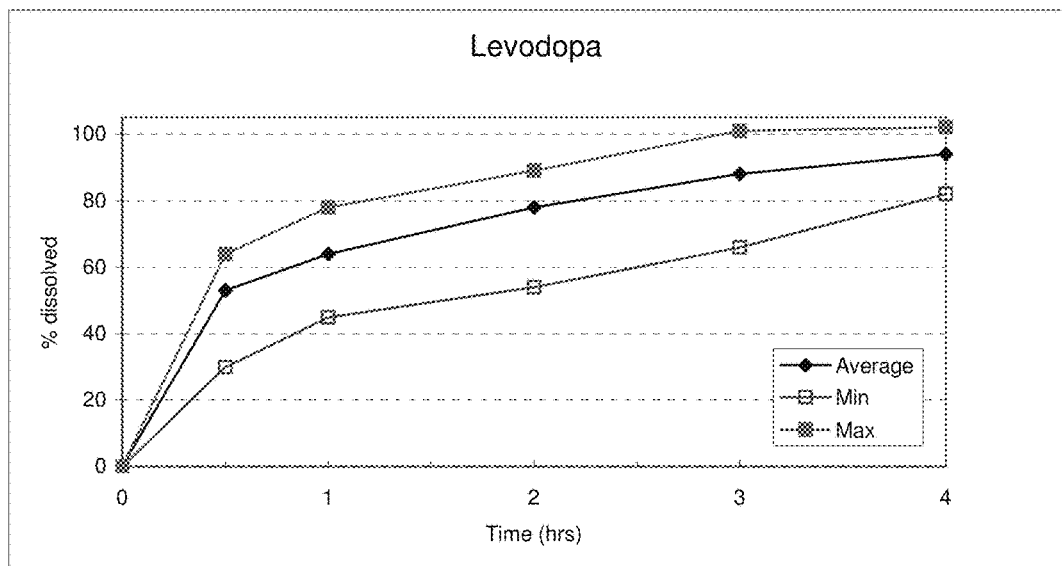
FIG. 21 depicts the in vitro release profile of levodopa from the exemplary multi-layered tablet of Example 4.
Figure 22:
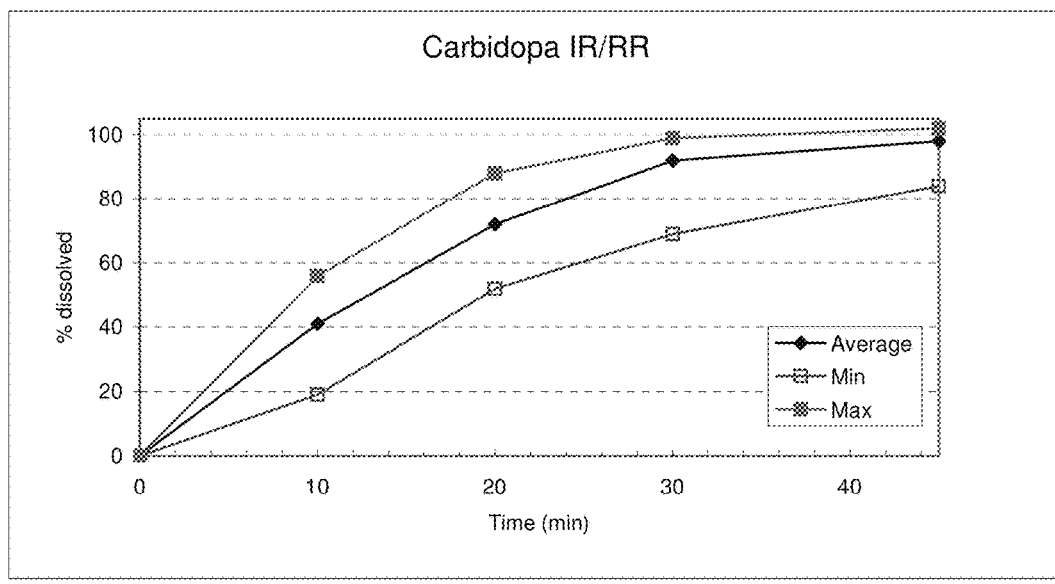
FIG. 22 depicts the in vitro release profile of carbidopa from the exemplary multi-layered tablet of Example 4.

FIGS. 20, 21, and 22 depict the release profile for formulations prepared as disclosed in Example 4. The in vitro testing is performed with USP Type II dissolution apparatus (paddles), in 900 ml of HCl 0.1N at 50 rpm maintained at a temperature of 37±0.5° C. The ropinirole release profile of the multi-layered tablets of Example 4 is disclosed in FIG. 20 and described as follows. The time is measured as from the instant that the tablet is initially placed in an aqueous environment.

| Time (hrs) | Average Released (%) | SD | Min | Max |
| --- | --- | --- | --- | --- |
| 0 | 0 | 0 | 0 | 0 |
| 1 | 7 | 7.5 | 0 | 20 |
| 2.5 | 35 | 9.0 | 16 | 50 |
| 4 | 62 | 10.2 | 43 | 78 |
| 6 | 80 | 8.2 | 56 | 94 |
| 8 | 86 | 5.6 | 70 | 101 |
| 12 | 89 | 4.2 | 75 | 102 |

The levodopa release profile of the multi-layered tablets of Example 4 is disclosed in FIG. 21 and described as follows. The time is measured as from the instant that the tablet is initially placed in an aqueous environment.

| Time (hrs) | Average Released (%) | SD | Min | Max |
| --- | --- | --- | --- | --- |
| 0 | 0 | 0 | 0 | 0 |
| 0.5 | 53 | 11.0 | 30 | 64 |
| 1 | 64 | 6.5 | 45 | 78 |
| 2 | 78 | 4.6 | 54 | 89 |
| 3 | 88 | 6.0 | 66 | 101 |
| 4 | 94 | 4.5 | 82 | 102 |

The carbidopa release profile of the multi-layered tablets of Example 4 is disclosed in FIG. 22 and described as follows. The time is measured as from the instant that the tablet is initially placed in an aqueous environment.

| Time (min) | Average Released (%) | SD | Min | Max |
| --- | --- | --- | --- | --- |
| 0 | 0 | 0 | 0 | 0 |
| 10 | 41 | 5.8 | 19 | 56 |
| 20 | 72 | 7.3 | 52 | 88 |
| 30 | 92 | 6.0 | 69 | 99 |
| 45 | 98 | 8.0 | 84 | 102 |

The combination of an atypical antipsychotic, with a serotonin reuptake inhibitor for treating psychosis with major depressive disorder, may help to find greater relief than using only an atypical antipsychotic agent. Combining venlafaxine and quetiapine may lead to an increase in improvement in patients not responding to one treatment approach alone; and adding ondansetron to the combination may help to avoid discontinuation of treatment do to nausea commonly caused by venlafaxine.

Example 5 discloses a multi-layered tablet comprising an osmotic core that provides venlafaxine CR, and an external IR or RR ondansetron-containing layer and an external ER quetiapine-containing layer in stacked arrangement with respect to and on opposite sides of the osmotic core.

Figure 23:
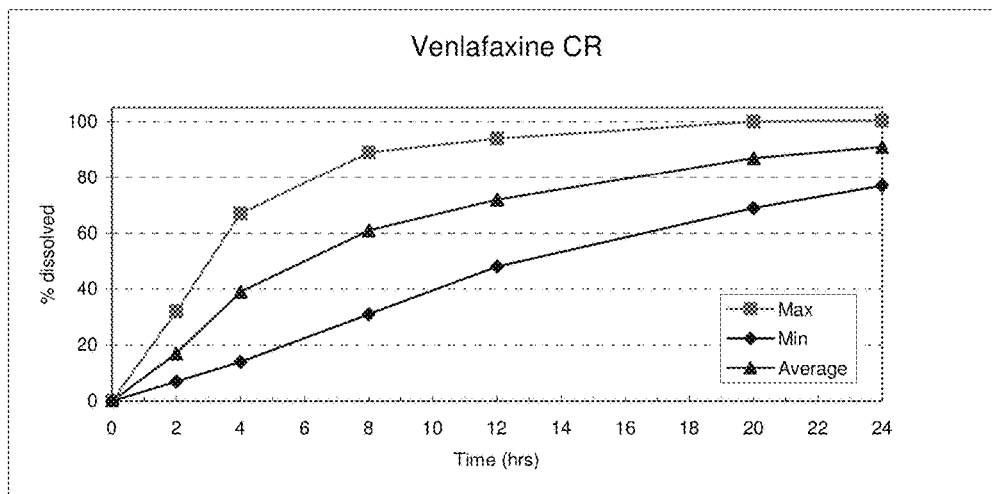
FIG. 23 depicts the in vitro release profile of venlafaxine from the exemplary multi-layered tablet of Example 5.
Figure 24:
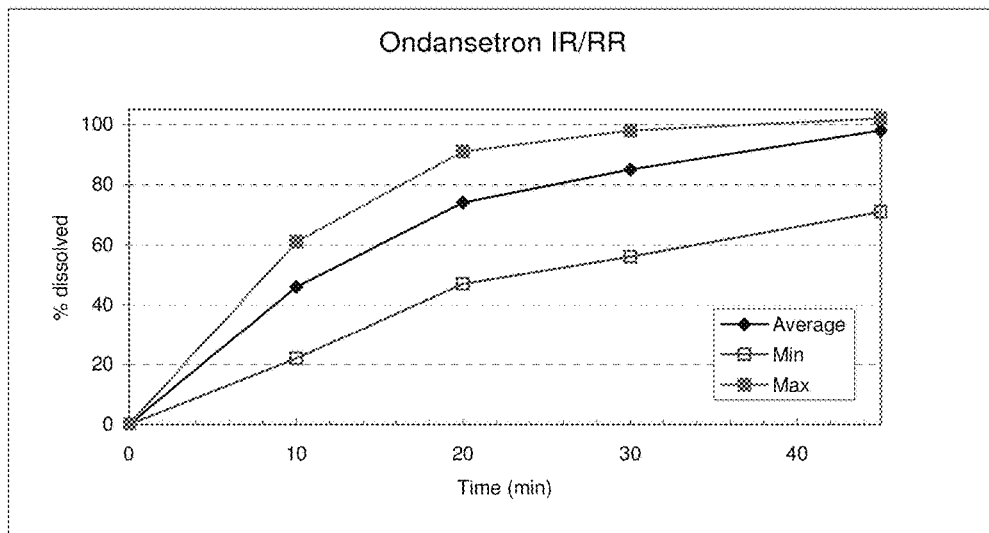
FIG. 24 depicts the in vitro release profile of ondansetron from the exemplary multi-layered tablet of Example 5.
Figure 25:
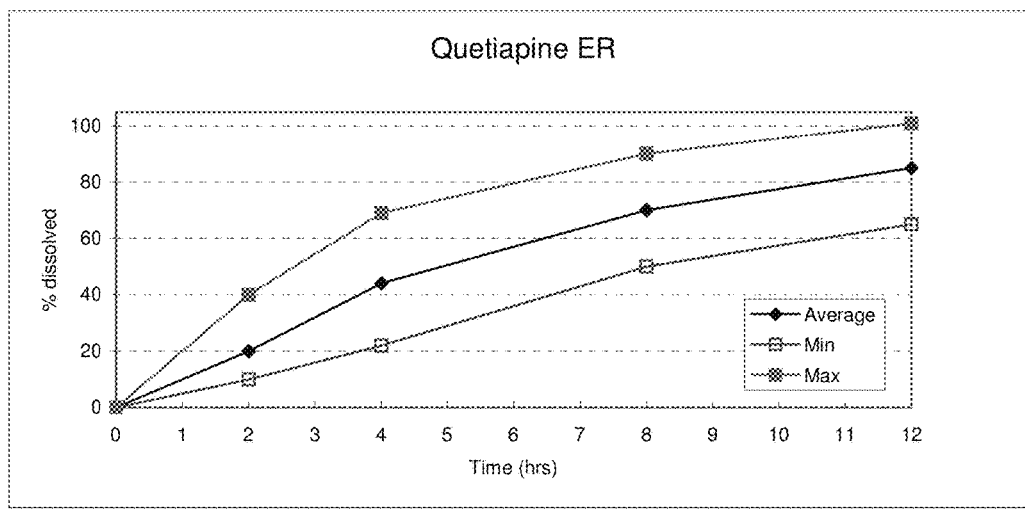
FIG. 25 depicts the in vitro release profile of quetiapine from the exemplary multi-layered tablet of Example 5.

FIGS. 23, 24, and 25 depict the release profile for formulations prepared as disclosed in Example 5. The in vitro testing is performed with USP Type II dissolution apparatus (paddles), in 900 ml of HCl 0.1N at 50 rpm maintained at a temperature of 37±0.5° C. The venlafaxine release profile of the multi-layered tablets of Example 5 is disclosed in FIG. 23 and described as follows. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 2 | 17 | 16.9 | 7 | 32 |
| 4 | 39 | 9.4 | 14 | 67 |
| 8 | 61 | 11.5 | 31 | 89 |
| 12 | 72 | 5.5 | 48 | 94 |
| 20 | 87 | 6.4 | 69 | 100 |
| 24 | 91 | 5.8 | 77 | 101 |

The ondansetron release profile of the multi-layered tablets of Example 5 is disclosed in FIG. 24 and described as follows. The time is measured as from the instant that the tablet is initially placed in an aqueous environment.

| Time (min) | Average Released (%) | SD | Min | Max |
|---|---|---|---|---|
| 0 | 0 | 0 | 0 | 0 |
| 10 | 46 | 4.7 | 22 | 61 |
| 20 | 74 | 7.8 | 47 | 91 |
| 30 | 85 | 7.9 | 56 | 98 |
| 45 | 98 | 8.2 | 71 | 102 |

The quetiapine release profile of the multi-layered tablets of Example 5 is disclosed in FIG. 25 and described as follows. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 2 | 20 | 6.4 | 10 | 40 |
| 4 | 44 | 6.2 | 22 | 69 |
| 8 | 70 | 5.7 | 50 | 90 |
| 12 | 85 | 6.8 | 65 | 101 |

Quetiapine is use for the treatment of acute manic episodes associated with bipolar I disorder, as either monotherapy or adjunct therapy to the mood stabilizers lithium or divalproex. Combining quetiapine and both, lithium and divalproex, may provide a more effective approach for the treatment of acute manic episodes.

Example 6 discloses a multi-layered tablet comprising an osmotic core that provides lithium ER, and an external IR or RR quetiapine-containing layer and an external ER divalproex sodium-containing layer in stacked arrangement with respect to and on opposite sides of the osmotic core.

Figure 26:
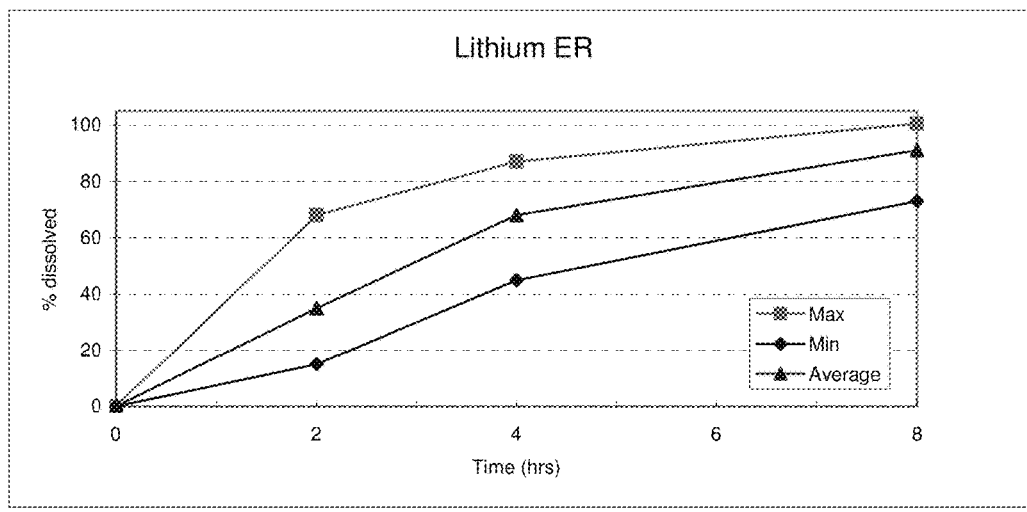
FIG. 26 depicts the in vitro release profile of lithium from the exemplary multi-layered tablet of Example 6.
Figure 27:
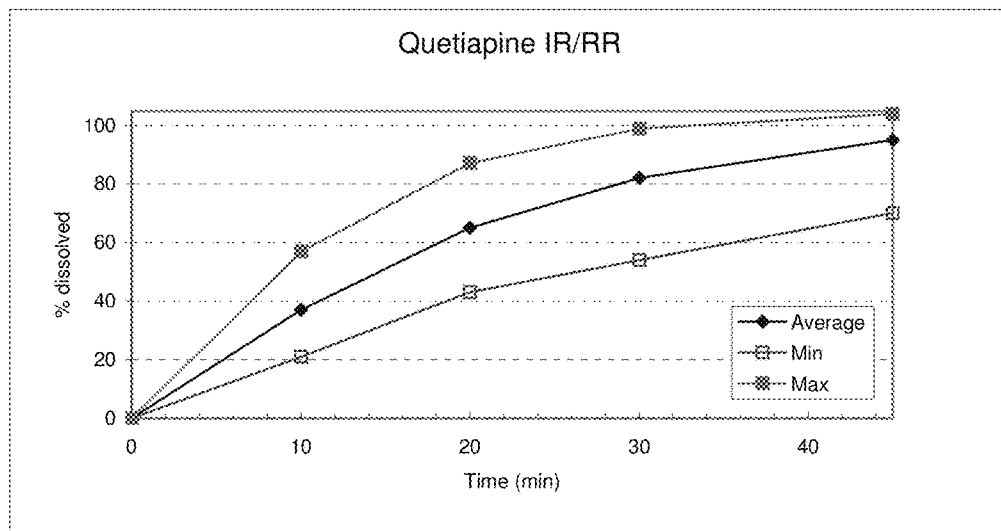
FIG. 27 depicts the in vitro release profile of quetiapine from the exemplary multi-layered tablet of Example 6.
Figure 28:
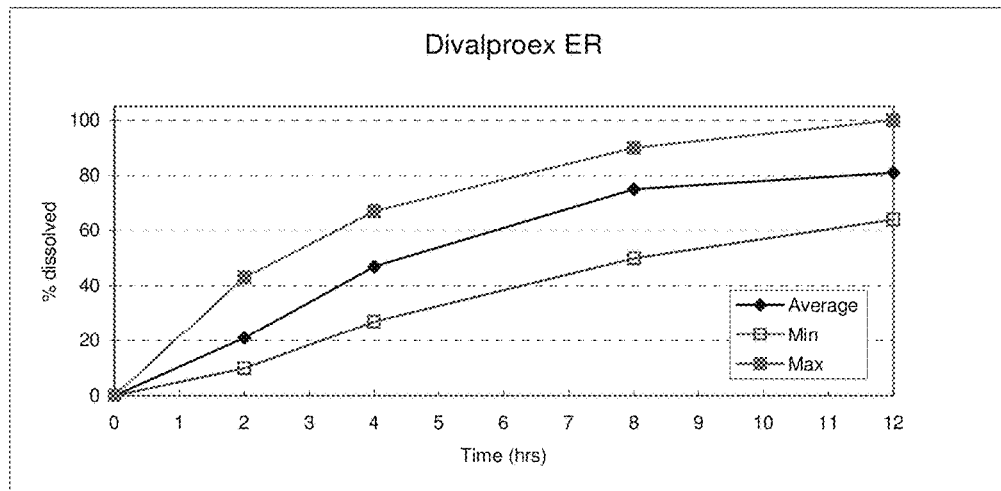
FIG. 28 depicts the in vitro release profile of divalproex sodium from the exemplary multi-layered tablet of Example 6.

FIGS. 26, 27, and 28 depict the release profile for formulations prepared as disclosed in Example 6. The in vitro testing is performed with USP Type II dissolution apparatus (paddles), in 900 ml of HCl 0.1N at 50 rpm maintained at a temperature of 37±0.5° C. The lithium release profile of the multi-layered tablets of Example 6 is disclosed in FIG. 26 and described as follows. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 2 | 35 | 16.9 | 15 | 68 |
| 4 | 68 | 9.4 | 45 | 87 |
| 8 | 91 | 5.8 | 73 | 101 |

The quetiapine release profile of the multi-layered tablets of Example 6 is disclosed in FIG. 27 and described as follows. The time is measured as from the instant that the tablet is initially placed in an aqueous environment.

| Time (min) | Average Released (%) | SD | Min | Max |
|---|---|---|---|---|
| 0 | 0 | 0 | 0 | 0 |
| 10 | 37 | 5.4 | 21 | 57 |
| 20 | 65 | 8.6 | 43 | 87 |
| 30 | 82 | 6.4 | 54 | 99 |
| 45 | 95 | 6.7 | 70 | 104 |

The divalproex sodium release profile of the multi-layered tablets of Example 6 is disclosed in FIG. 28 and described as follows. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 2 | 21 | 7.4 | 10 | 43 |
| 4 | 47 | 5.6 | 27 | 67 |
| 8 | 75 | 5.9 | 50 | 90 |
| 12 | 81 | 4.8 | 64 | 100 |

Examples 9 discloses a multi-layered tablet comprising a gastro-resistant coated core that provides a delayed and extended release of levodopa, and an external IR or RR of carbidopa-containing layer, and an external ER entacapone-containing layer in stacked arrangement with respect to and on opposite sides of the gastro-resistant coated core.

Figure 29:
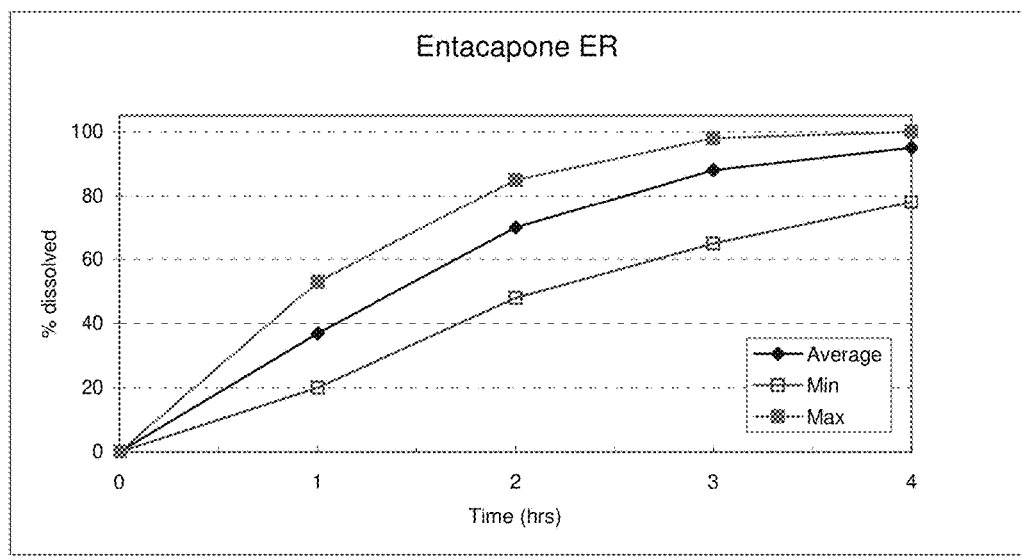
FIG. 29 depicts the in vitro release profile of entacapone from the exemplary multi-layered tablet of Example 9.
Figure 30:
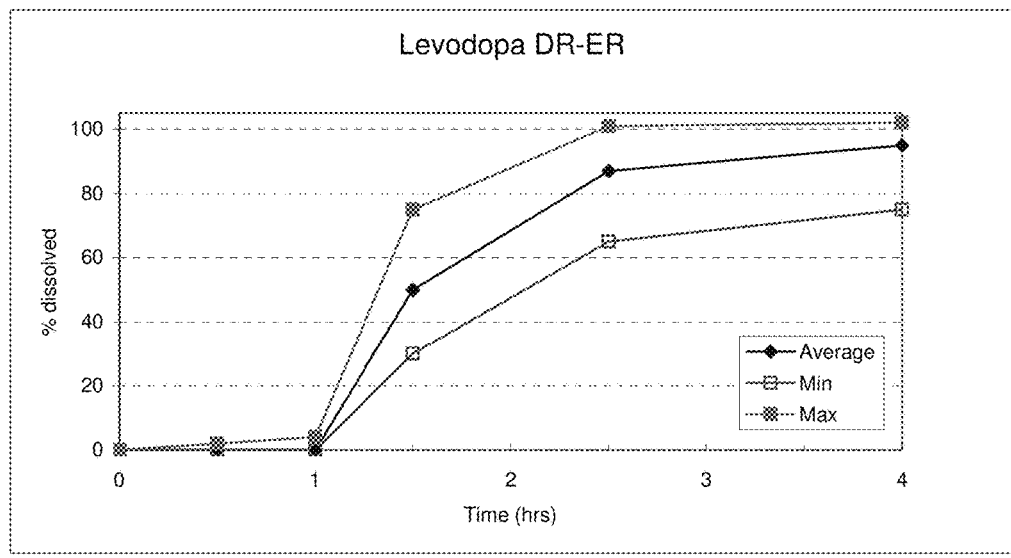
FIG. 30 depicts the in vitro release profile of levodopa from the exemplary multi-layered tablet of Example 9.
Figure 31:
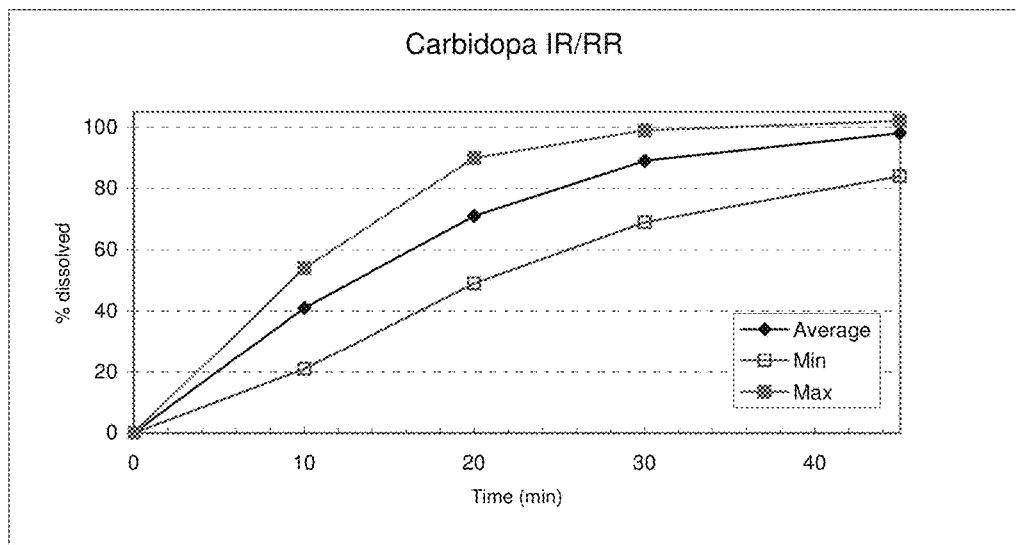
FIG. 31 depicts the in vitro release profile of carbidopa from the exemplary multi-layered tablet of Example 9.

FIGS. 29, 30, and 31 depict the release profile for formulations prepared as disclosed in Example 9. The entacapone release profile of the multi-layered tablets of Example 9 is described as follows and disclosed in FIG. 29. The in vitro testing is performed with USP Type III dissolution apparatus, in 250 ml of USP phosphate buffer pH 6.8 with 1% tween. The samples were tested by high pressure liquid chromatography. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 1 | 37 | 7.8 | 20 | 53 |
| 2 | 70 | 6.9 | 48 | 85 |
| 3 | 88 | 6.8 | 65 | 98 |
| 4 | 95 | 7.8 | 78 | 100 |

The levodopa release profile of the multi-layered tablets of Example 9 is described as follows and disclosed in FIG. 30. The in vitro testing is performed with USP Type II dissolution apparatus (paddles), first in 900 ml of HCl 0.1N maintained at a temperature of 37±0.5° C., during 1 hour, and then the medium is adjusted to pH 6 with 1% tween. The samples were tested by high pressure liquid chromatography. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 0.5 | 0 | 15.0 | 0 | 2 |
| 1 | 0 | 18.0 | 0 | 4 |
| 1.5 | 50 | 15.4 | 30 | 75 |
| 2.5 | 87 | 7.5 | 65 | 101 |
| 4 | 95 | 5.3 | 75 | 102 |

The carbidopa release profile of the multi-layered tablets of Example 9 is described as follows and disclosed in FIG. 31. The time is measured as from the instant that the tablet is initially placed in an aqueous environment.

| Time (min) | Average Released (%) | SD | Min | Max |
|---|---|---|---|---|
| 0 | 0 | 0 | 0 | 0 |
| 10 | 41 | 5.4 | 21 | 54 |
| 20 | 71 | 6.5 | 49 | 90 |
| 30 | 89 | 6.9 | 69 | 99 |
| 45 | 98 | 5.4 | 84 | 102 |

Example 10 discloses a multi-layered tablet comprising a gastro-resistant coated core that provides a delayed and extended release of levodopa, and an external IR or RR levodopa/carbidopa-containing layer and an external ER entacapone-containing layer in stacked arrangement with respect to and on opposite sides of the gastro-resistant coated core.

Figure 32:
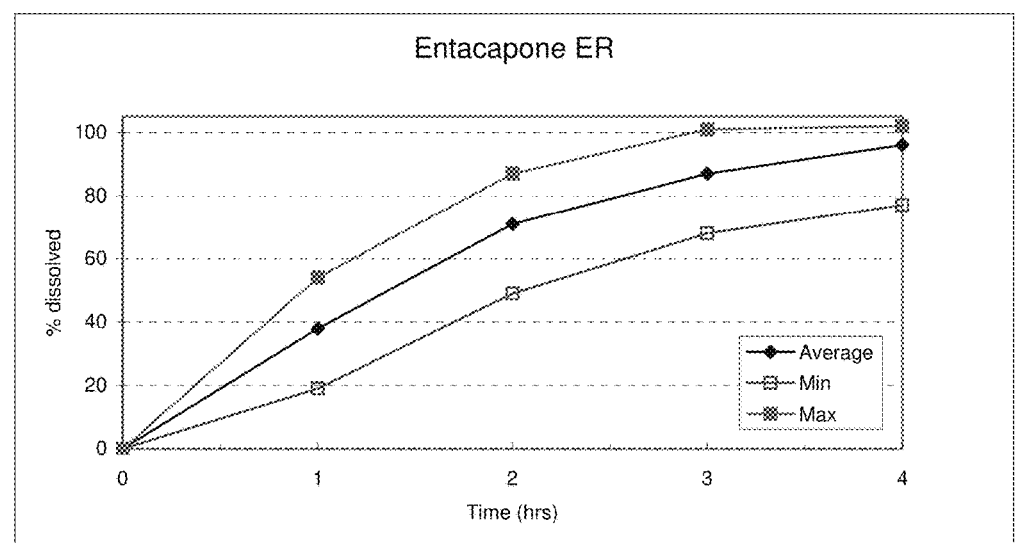
FIG. 32 depicts the in vitro release profile of entacapone from the exemplary multi-layered tablet of Example 10.
Figure 33:
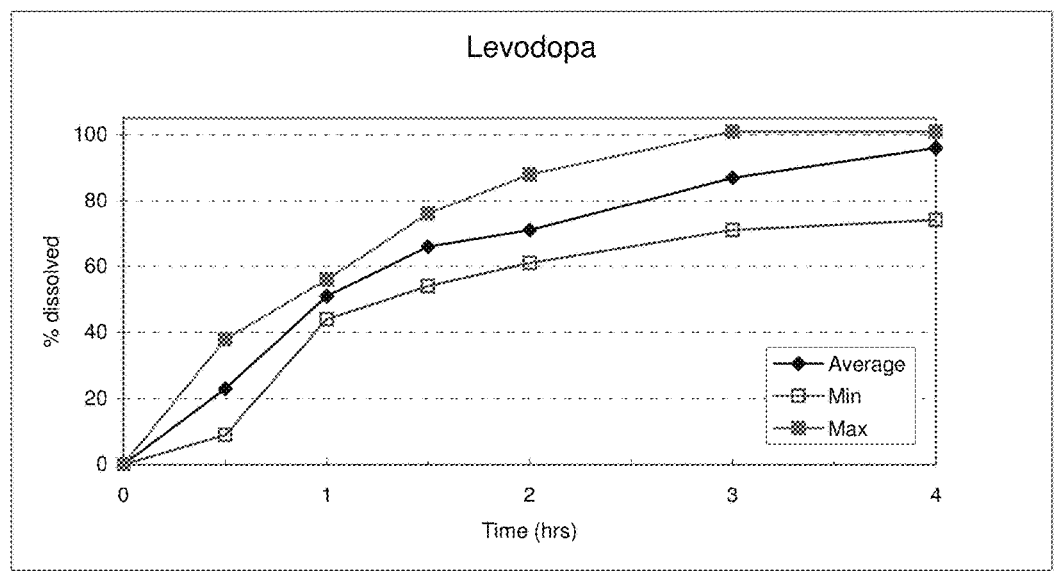
FIG. 33 depicts the in vitro release profile of levodopa from the exemplary multi-layered tablet of Example 10.
Figure 34:
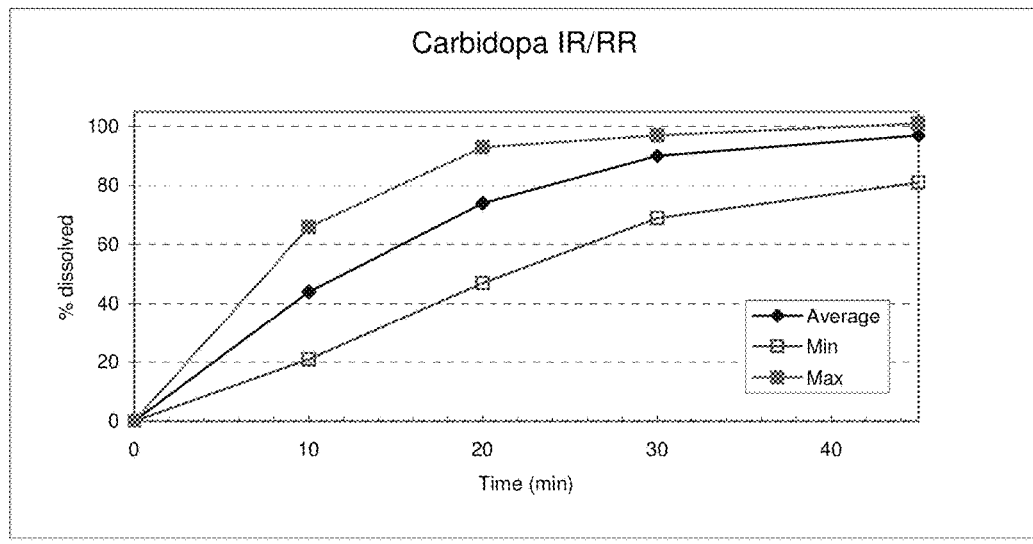
FIG. 34 depicts the in vitro release profile of carbidopa from the exemplary multi-layered tablet of Example 10.

FIGS. 32, 33, and 34 depict the release profile for formulations prepared as disclosed in Example 10. The entacapone release profile of the multi-layered tablets of Example 10 is described as follows and disclosed in FIG. 32. The in vitro testing is performed with USP Type III dissolution apparatus, in 250 ml of USP phosphate buffer pH 6.8 with 1% tween. The samples were tested by high pressure liquid chromatography. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 1 | 38 | 8.4 | 19 | 54 |
| 2 | 71 | 6.5 | 49 | 87 |
| 3 | 87 | 5.7 | 68 | 101 |
| 4 | 96 | 8.5 | 77 | 102 |

The levodopa release profile of the multi-layered tablets of Example 10 is described as follows and disclosed in FIG. 33. The in vitro testing is performed with USP Type II dissolution apparatus (paddles), first in 900 ml of HCl 0.1N maintained at a temperature of 37±0.5° C., during 1 hour, and then the medium is adjusted to pH 6 with 1% tween. The samples were tested by high pressure liquid chromatography. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 0.5 | 23 | 6.5 | 9 | 38 |
| 1 | 51 | 7.2 | 44 | 56 |
| 1.5 | 66 | 6.6 | 54 | 76 |
| 2 | 71 | 7.1 | 61 | 88 |
| 3 | 87 | 7.4 | 71 | 101 |
| 4 | 96 | 5.4 | 74 | 101 |

The carbidopa release profile of the multi-layered tablets of Example 10 is described as follows and disclosed in FIG. 34. The time is measured as from the instant that the tablet is initially placed in an aqueous environment.

| Time (min) | Average Released (%) | SD | Min | Max |
|---|---|---|---|---|
| 0 | 0 | 0 | 0 | 0 |
| 10 | 44 | 4.2 | 21 | 66 |
| 20 | 74 | 6.7 | 47 | 93 |
| 30 | 90 | 8.9 | 69 | 97 |
| 45 | 97 | 5.5 | 81 | 101 |

Naproxen is an arylacetic acid with analgesic and antipyretic properties, member of the group of nonsteroidal anti-inflammatory drugs (NSAIDs). The mechanism of action is related to prostaglandin synthetase inhibition. Ergotamine is an alpha adrenergic blocking agent with a direct stimulating effect on the smooth muscle of peripheral and cranial blood vessels and produces depression of central vasomotor centers. Domperidone is a dopamine-receptor blocking agent that does not cross the blood-brain barrier and its action in the chemo-emetic trigger zone produces an anti-emetic effect. The combination of naproxen, ergotamine and domperidone would provide a symptomatic treatment for the acute migraine attack, based on a consistent dose of a pain reliever, such as naproxen, that will be enhance by the vasoconstrictor properties of an ergot alkaloid, such as ergotamine. The co-administration of an antiemetic drug, such as domperidone, that also increases gastric motility, is likely to facilitate the absorption of the other drugs and, at the same time, to diminish associated migraine symptoms, such as nausea and vomiting, helping to ameliorate the attack.

Example 11 discloses a multi-layered tablet comprising an osmotic core that provides domperidone ER, and an external IR or RR ergotamine-containing layer and an external ER naproxen-containing layer in stacked arrangement with respect to and on opposite sides of the osmotic core.

Figure 35:
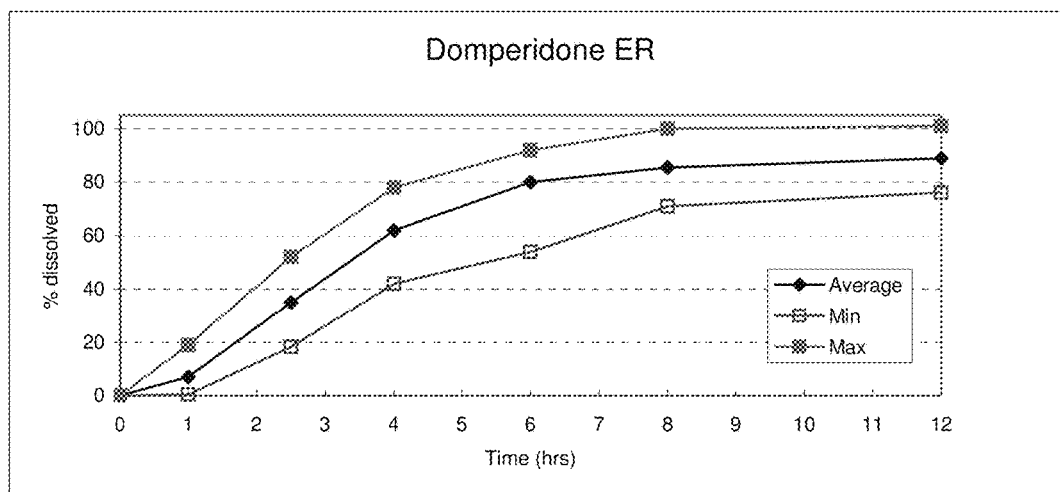
FIG. 35 depicts the in vitro release profile of domperidone from the exemplary multi-layered tablet of Example 11
Figure 36:
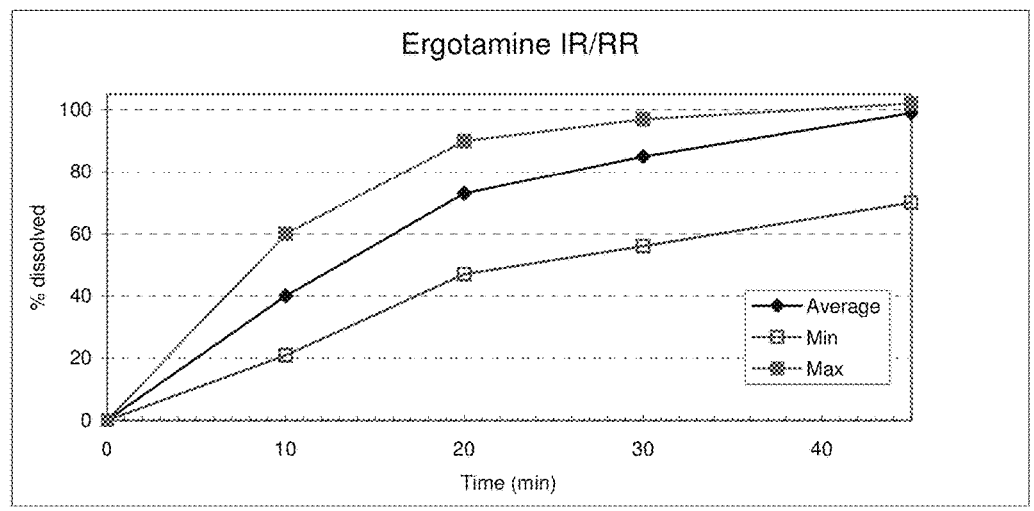
FIG. 36 depicts the in vitro release profile of ergotamine from the exemplary multi-layered tablet of Example 11
Figure 37:
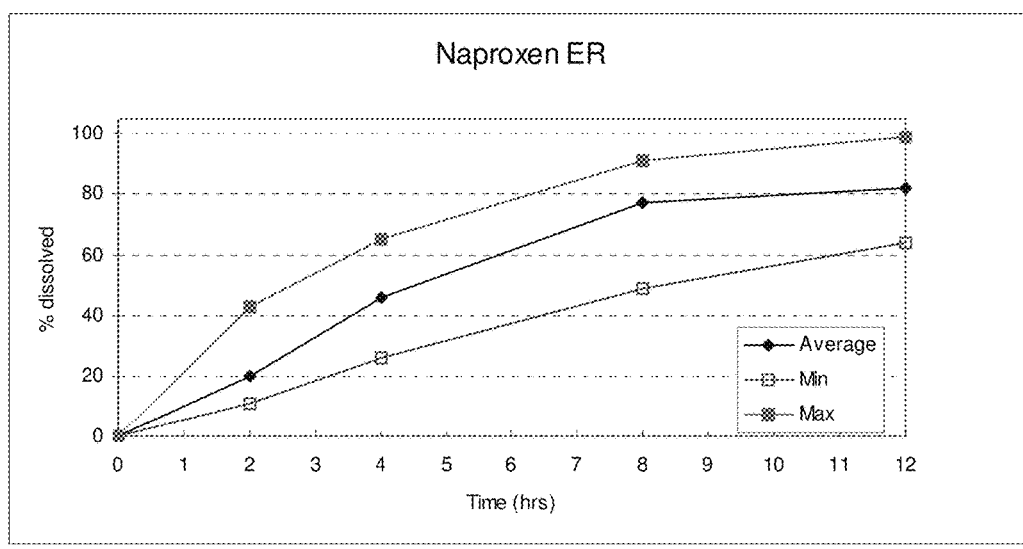
FIG. 37 depicts the in vitro release profile of naproxen from the exemplary multi-layered tablet of Example 11

FIGS. 35, 36, and 37 depict the release profile for formulations prepared as disclosed in Example 11. The in vitro testing is performed with USP Type II dissolution apparatus (paddles), in 900 ml of HCl 0.1N at 50 rpm maintained at a temperature of 37±0.5° C. The domperidone release profile of the multi-layered tablets of Example 11 is disclosed in FIG. 35 and described as follows. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 1 | 7 | 7.3 | 0 | 19 |

-continued

| Time (hrs) | Average Released (%) | SD | Min | Max |
|---|---|---|---|---|
| 2.5 | 35 | 9.1 | 18 | 52 |
| 4 | 62 | 9.9 | 42 | 78 |
| 6 | 80 | 8.5 | 54 | 92 |
| 8 | 86 | 5.4 | 71 | 100 |
| 12 | 89 | 4.0 | 76 | 101 |

The ergotamine release profile of the multi-layered tablets of Example 11 is disclosed in FIG. 36 and described as follows. The time is measured as from the instant that the tablet is initially placed in an aqueous environment.

| Time (min) | Average Released (%) | SD | Min | Max |
|---|---|---|---|---|
| 0 | 0 | 0 | 0 | 0 |
| 10 | 40 | 4.5 | 21 | 60 |
| 20 | 73 | 7.6 | 47 | 90 |
| 30 | 85 | 7.8 | 56 | 97 |
| 45 | 99 | 8.0 | 70 | 102 |

The naproxen release profile of the multi-layered tablets of Example 11 is disclosed in FIG. 37 and described as follows. The time is measured as from the instant that the tablet is initially placed in an aqueous environment.

| Time (hrs) | Average Released (%) | SD | Min | Max |
|---|---|---|---|---|
| 0 | 0 | 0 | 0 | 0 |
| 2 | 20 | 7.0 | 11 | 43 |
| 4 | 46 | 5.4 | 26 | 65 |
| 8 | 77 | 5.8 | 49 | 91 |
| 12 | 82 | 4.5 | 64 | 99 |

The following examples should not be considered exhaustive, but merely illustrative of only a few of the many embodiments contemplated by the present invention. The methods described herein can be followed to prepare tablets according to the invention.

Example 1

The following procedure is used to prepare a multi-layered tablet comprising an osmotic device (intermediate drug-containing composition) that provides amantadine ER, and an external IR or RR levodopa/carbidopa-containing layer and an external ER levodopa-containing layer in stacked arrangement with respect to and on opposite sides of the osmotic core. An exemplary formulation is disclosed below.

| Ingredients/functional category | Amount (mg) |
|---|---|
| Osmotic device | |
| Core | |
| Amantadine HCl | 160 |
| Filler 1 | 10.0-50.0 |
| Binder | 5.0-15.0 |
| Glidant | 0.15-3.0 |
| Lubricant | 0.5-5.0 |
| Osmotic agent | 0-75 |
| Filler 2 | 5.0-30.0 |
| Semipermeable Membrane | |
| Cellulose ester 1 | 0-30.0 |
| Cellulose ester 2 | 0-30.0 |
| Plasticizer | 0.3-1.5 |
| Dry Coating | |
| Layer A (IR/RR) | |
| Levodopa | 100.0 |
| Carbidopa | 50.0 |
| Filler 1 | 20.0-300.0 |
| Filler 2 | 20.0-300.0 |
| Binder | 5.0-50.0 |
| Disintegrant | 5.0-20.0 |
| Glidant | 0.2-5.0 |
| Lubricant | 1.0-5.0 |
| Layer B (ER) | |
| Levodopa | 100.0 |
| ER Polymer | 1.0-10.0 |
| Filler 1 | 20.0-300.0 |
| Filler 2 | 20.0-300.0 |
| Plasticizer | 10.0-50.0 |
| Inorganic salt | 1.0-30.0 |
| Glidant | 0.2-5.0 |
| Lubricant | 1.0-5.0 |

Amantadine hydrochloride, filler 1, filler 2, and a binder, are first individually screened to a uniform size using a Quadro Comil at less than 500 rpm, and then mixed with osmotic agent previously milled using a Fitz Mill with a screen 0020-0069 at less than 8000 rpm, in a mixer granulator for up to 5 minutes to form a homogenous powder blend. The granulation process is initiated by the gradual addition of purified water to the powder blend, with continuous mixing, to change the consistency of the dry powder ingredients to granules. The wet granulation is sieved through a Quadro Comil at a speed less than 500 rpm, and then dried in a static bed at 50° C. for humidity reduction. Next, the dry granules are milled using a Quadro Comil with a screen R991µ at less than 2,000 rpm for size reduction. Then, a mixture of a glidant and a lubricant, previously sieved through a 60-mesh screen, is added and mixed for about 5 minutes. The resulting mixture is compressed in a compressor with 7-10 mm diameter punches to form uncoated cores.

A semipermeable membrane composition is prepared as follows: cellulose ester 1, cellulose ester 2, and a plasticizer of low molecular weight are blended in acetone and purified water. The blend is sprayed onto the uncoated cores to obtain coated cores. The semipermeable membrane weight range is approximately between 8 and 20 mg. The coated cores are then perforated with a laser equipment to form at least one passageway of 0.2-0.8 mm of diameter.

The IR/RR composition (layer A) is prepared as follows: the levodopa, carbidopa, filler 1, filler 2, binder and half of the disintegrant are first individually screened in a rotary mill with a 991 µm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 µm screen at less than 1200 rpm for size reduction. Then, glidant, lubricant, and the other half of the disintegrant, previously sieved through a 30-mesh screen, are added and mixed for about 5 minutes to obtain the IR/RR composition.

The ER layer (layer B) composition is prepared as follows: the levodopa and ER polymer are first individually screened in a rotary mill with a 991 μm screen, and then mixed with filler 1, filler 2 and inorganic salt previously milled using a hammer mill with a 0020 screen, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, plasticizer and lubricant, previously sieved through a 30-mesh screen, are added and mixed for about 5 minutes to obtain the ER layer composition.

The multi-layered tablets are manufactured as follows: the IR/RR composition is loaded into the first hopper (first filled position) of the tableting machine, the ER composition is loaded into the second hopper (second filled position) of the tableting machine, and the osmotic cores are placed into the internal core dispenser. The die is first filled with 200-850 mg of IR/RR composition, and then the osmotic core is dispensed onto the first composition. After that the die is filled with 150-800 mg of ER composition and finally all the components are compressed to obtained the multi-layered tablets.

Example 2

The following procedure is used to prepare a multi-layered tablet comprising a gastro-resistant coated core (exemplary intermediate drug-containing composition) that provides a delayed and extended release of levodopa, and an external IR or RR levodopa/carbidopa-containing layer and an external ER amantadine-containing layer in stacked arrangement with respect to and on opposite sides of the gastro-resistant coated core. An exemplary formulation is disclosed below.

| Ingredients/functional category | Amount (mg) |
|---|---|
| Gastro-resistant coated core | |
| Core (ER) | |
| Levodopa | 100.0 |
| Filler | 5.0-100.0 |
| CR polymer | 1.0-20.0 |
| Glidant | 0.2-5.0 |
| Lubricant | 1.0-5.0 |
| Enteric coating (DR) | |
| Enteric film polymer | 5.0-200.0 |
| Plasticizer (optional) | 0.1-20.0 |
| Plasticizer | 0.3-1.5 |
| Dry Coating | |
| Layer A (IR/RR) | |
| Levodopa | 100.0 |
| Carbidopa | 50.0 |
| Filler 1 | 20.0-300.0 |
| Filler 2 | 20.0-300.0 |
| Binder | 5.0-50.0 |
| Disintegrant | 5.0-20.0 |

-continued

| Ingredients/functional category | Amount (mg) |
|---|---|
| Glidant | 0.2-5.0 |
| Lubricant | 1.0-5.0 |
| Layer B (ER) | |
| Amantadine | 160.0 |
| CR Polymer | 1.0-10.0 |
| Filler 1 | 20.0-300.0 |
| Filler 2 | 20.0-300.0 |
| Plasticizer | 10.0-50.0 |
| Inorganic salt | 1.0-30.0 |
| Glidant | 0.2-5.0 |
| Lubricant | 1.0-5.0 |

The ER core composition is prepared as follows: the levodopa and CR polymer are first individually screened in a rotary mill with a 991 μm screen, and then mixed with filler, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant and the lubricant, previously sieved through a 30-mesh screen, are added and mixed for about 5 minutes. The final blend is tabletted to provide the cores.

The enteric coating composition is prepared as follows: the enteric film polymer, and the plasticizer are blended in purified water to form a polymer suspension. This suspension is sprayed onto the cores in a perforated pan coater to obtain gastro-resistant coated cores.

The IR/RR composition (layer A) is prepared as follows: the levodopa, carbidopa, filler 1, filler 2, binder, and half of the disintegrant are first individually screened in a rotary mill with a 991 μm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, lubricant, and the other half of the disintegrant, previously sieved through a 30-mesh screen, are added and mixed for about 5 minutes to obtain the IR/RR composition.

The ER layer (layer B) composition is prepared as follows: amantadine and the CR polymer are first individually screened in a rotary mill with a 991 μm screen, and then mixed with filler 1, filler 2 and inorganic salt previously milled using a hammer mill with a 0020 screen, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, plasticizer, and lubricant, previously sieved through a 30-mesh screen, are added and mixed for about 5 minutes to obtain the ER composition.

The multi-layered tablets are manufactured as follows: the IR/RR composition is loaded into the first hopper (first filled position) of the tableting machine, the ER composition is loaded into the second hopper (second filled position) of the tableting machine, and the dry gastro-resistant coated cores are placed into the internal core dispenser. The die is first filled with 200-830 mg of IR/RR composition, and then the gastro-resistant coated core is dispensed onto the first composition. After that the die is filled with 200-860 mg of ER composition and finally all the components are compressed to obtained the multi-layered tablets.

Example 3

The following procedure is used to prepare a multi-layered tablet comprising an osmotic device that provides venlafaxine CR, and an external IR or RR ondansetron-containing layer and an external ER alprazolam-containing layer in stacked arrangement with respect to and on opposite sides of the osmotic core. An exemplary formulation is disclosed below.

| Ingredients/functional category | Amount (mg) |
| --- | --- |
| Osmotic device | |
| Core | |
| Venlafaxine Hydrochloride | 169.72 |
| Filler | 30.0-100.0 |
| Osmotic salt | 10.0-80.0 |
| Binder | 10.0-30.0 |
| Plasticizer 1 | 1.0-5.0 |
| Glidant | 2.0-10.0 |
| Plasticizer 2 | 20.0-50.0 |
| Lubricant | 2.0-15.00 |
| Semipermeable Membrane | |
| Cellulose ester | 1.0-100.0 |
| Plasticizer | 2.0-10.0 |
| Dry Coating | |
| Layer A (IR/RR) | |
| Ondansetron HCl•2H2O | 5.0 |
| Filler 1 | 50.0-200.0 |
| Filler 2 | 50.0-200.0 |
| Binder | 4.0-40.0 |
| Disintegrant | 3.0-20.0 |
| Glidant | 0.2-5.0 |
| Lubricant | 1.0-5.0 |
| Layer B (ER) | |
| Alprazolam | 1.0 |
| ER Polymer | 1.0-10.0 |
| Filler 1 | 50.0-200.0 |
| Filler 2 | 50.0-200.0 |
| Plasticizer | 10.0-70.0 |
| Inorganic Salt | 1.0-40.0 |
| Glidant | 0.2-5.0 |
| Lubricant | 1.0-10.0 |

Venlafaxine hydrochloride, the filler, and the binder, are first individually screened to a uniform size using a Quadro Comil at less than 1,000 rpm, and then mixed with the osmotic salt previously milled using a Fitz Mill with a screen 0020-0069 at less than 8000 rpm, in a mixer granulator for up to 25 minutes to form a homogenous powder blend. The granulation process is initiated by adding a solution containing a plasticizer of low molecular weight and a plasticizer of higher molecular weight in purified water for granules. The wet granulation is sieved through a Quadro Comil at a speed less than 1000 rpm, and then dried in a static bed at 50° C. for humidity reduction. Next, the dry granules are milled using a Quadro Comil with a screen R991µ at less than 2,000 rpm for size reduction. Then, a mixture of the glidant and the lubricant, previously sieved through a 100-mesh screen, is added and mixed for about 15 minutes. The resulting mixture is compressed in a compressor with 8.0 mm diameter punches to form uncoated cores.

A semipermeable membrane composition is prepared as follows: cellulose ester, and the plasticizer of low molecular weight are blended in a mixture of solvents. The blend is sprayed onto the uncoated cores to obtain coated cores. The coated cores are then perforated with a laser equipment to form at least one passageway of 0.2-0.8 mm of diameter.

The immediate or rapid release composition (layer A) is prepared as follows: the ondansetron, filler 1, filler 2, binder and half of the disintegrant are first individually screened in a rotary mill with a 991 µm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 µm screen at less than 1200 rpm for size reduction. Then, glidant, lubricant and the other half of the disintegrant, previously sieved through a 30-mesh screen, are added and mixed for about 5 minutes.

The extended release layer (layer B) composition is prepared as follows: alprazolam and ER polymer are first individually screened in a rotary mill with a 991 µm screen, and then mixed with filler 1, filler 2 and inorganic salt previously milled using a hammer mill with a 0020 screen, in a mixer granulator for up to 10 minutes to form a homogenous powder blend. The granulation process was initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 µm screen at less than 1200 rpm for size reduction. Then, the glidant, plasticizer and lubricant, previously sieved through a 30-mesh screen, are added and mixed for about 5 minutes.

The multi-layered tablets are manufactured as follows: the IR/RR composition is loaded into the first hopper (first filled position) of the tableting machine, the ER composition is loaded into the second hopper (second filled position) of the tableting machine, and the osmotic cores are placed into the internal core dispenser. The die is first filled with 100-500 mg of IR/RR composition, and then the osmotic core is dispensed onto the first composition. After that the die is filled with 100-540 mg of ER composition and finally all the components are compressed to obtained the multi-layered tablets.

Example 4

The following procedure is used to prepare a multi-layered tablet comprising an osmotic device that provides ropinirole CR, and an external IR or RR levodopa/carbidopa-containing layer and an external ER levodopa-containing layer in stacked arrangement with respect to and on opposite sides of the osmotic core. An exemplary formulation is disclosed below.

| Ingredients/functional category | Amount (mg) |
|---|---|
| Osmotic device Core | |
| Ropinirole | 3.0 |
| Filler 1 | 10.0-50.0 |
| Binder | 5.0-15.0 |
| Glidant | 0.15-3.0 |
| Lubricant | 0.5-5.0 |
| Osmotic agent | 0-75 |
| Filler 2 | 5.0-30.0 |
| Semipermeable Membrane | |
| Cellulose ester 1 | 0-30.0 |
| Cellulose ester 2 | 0-30.0 |
| Plasticizer | 0.3-1.5 |
| Dry Coating Layer A (IR/RR) | |
| Levodopa | 100.0 |
| Carbidopa | 50.0 |
| Filler 1 | 20.0-300.0 |
| Filler 2 | 20.0-300.0 |
| Binder | 5.0-50.0 |
| Disintegrant | 5.0-20.0 |
| Glidant | 0.2-5.0 |
| Lubricant | 1.0-5.0 |
| Layer B (ER) | |
| Levodopa | 100.0 |
| ER Polymer | 1.0-10.0 |
| Filler 1 | 20.0-300.0 |
| Filler 2 | 20.0-300.0 |
| Plasticizer | 10.0-50.0 |
| Inorganic salt | 1.0-30.0 |
| Glidant | 0.2-5.0 |
| Lubricant | 1.0-5.0 |

Ropinirole, filler 1, filler 2, and the binder, are first individually screened to a uniform size using a Quadro Comil at less than 500 rpm, and then mixed with the osmotic agent previously milled using a Fitz Mill with a screen 0020-0069 at less than 8000 rpm, in a mixer granulator for up to 5 minutes to form a homogenous powder blend. The granulation process is initiated by the gradual addition of purified water to the powder blend, with continuous mixing, to change the consistency of the dry powder ingredients to granules. The wet granulation is sieved through a Quadro Comil at a speed less than 500 rpm, and then dried in a static bed at 50°C for humidity reduction. Next, the dry granules are milled using a Quadro Comil with a screen R991μ at less than 2,000 rpm for size reduction. Then, a mixture of the glidant and lubricant, previously sieved through a 60-mesh screen, is added and mixed for about 5 minutes. The resulting mixture is compressed in a compressor with 7-10 mm diameter punches to form uncoated cores.

A semipermeable membrane composition is prepared as follows: cellulose ester 1, cellulose ester 2, and the plasticizer of low molecular weight are blended in acetone and purified water. The blend is sprayed onto the uncoated cores to obtain coated cores. The semipermeable membrane weight range is approximately between 8 and 20 mg. The membrane coating of each core is then perforated with laser equipment to form at least one passageway of 0.2-0.8 mm through the semipermeable coat.

The immediate or rapid release composition (layer A) is prepared as follows: the levodopa, carbidopa, filler 1, filler 2, the binder and half of the disintegrant are first individually screened in a rotary mill with a 991 μm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, lubricant and the other half of the disintegrant, previously sieved through a 30-mesh screen, are added and mixed for about 5 minutes.

The extended release layer (layer B) composition is prepared as follows: the levodopa and ER polymer are first individually screened in a rotary mill with a 991 μm screen, and then mixed with filler 1, filler 2, and the inorganic salt previously milled using a hammer mill with a 0020 screen, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, plasticizer, and lubricant, previously sieved through a 30-mesh screen, are added and mixed for about 5 minutes.

The multi-layered tablets are manufactured as follows: the IR/RR composition is loaded into the first hopper (first filled position) of the tableting machine, the ER composition is loaded into the second hopper (second filled position) of the tableting machine, and the osmotic cores are placed into the internal core dispenser. The die is first filled with 200-830 mg of IR/RR composition, and then the osmotic core is dispensed onto the first composition. After that the die is filled with 150-800 mg of ER composition and finally all the components are compressed to obtained the multi-layered tablets.

Example 5

The following procedure is used to prepare a multi-layered tablet comprising an osmotic device that provides venlafaxine CR, and an external IR or RR ondansetron-containing layer and an external ER quetiapine-containing layer in stacked arrangement with respect to and on opposite sides of the osmotic core. An exemplary formulation is disclosed below.

| Ingredients/functional category | Amount (mg) |
|---|---|
| Osmotic device Core | |
| Venlafaxine Hydrochloride | 169.72 |
| Filler | 30.0-100.0 |
| Osmotic agent | 10.0-80.0 |
| Binder | 10.0-30.0 |
| Plasticizer 1 | 1.0-5.0 |
| Glidant | 2.0-10.0 |
| Plasticizer 2 | 20.0-50.0 |
| Lubricant | 2.0-15.00 |
| Semipermeable Membrane | |
| Cellulose ester | 1.0-100.0 |
| Plasticizer | 2.0-10.0 |
| Dry Coating Layer A (IR/RR) | |
| Ondansetron HCl•2H2O | 5.0 |
| Filler 1 | 50.0-200.0 |
| Filler 2 | 50.0-200.0 |

-continued

| Ingredients/functional category | Amount (mg) |
|---|---|
| Binder | 4.0-40.0 |
| Disintegrant | 3.0-20.0 |
| Glidant | 0.2-5.0 |
| Lubricant | 1.0-5.0 |
| Layer B (ER) | |
| Quetiapine | 100.0 |
| ER Polymer | 1.0-10.0 |
| Filler 1 | 20.0-300.0 |
| Filler 2 | 20.0-300.0 |
| Plasticizer | 10.0-50.0 |
| Inorganic salt | 1.0-30.0 |
| Glidant | 0.2-5.0 |
| Lubricant | 1.0-5.0 |

Venlafaxine hydrochloride, a filler, and a binder, are first individually screened to a uniform size using a Quadro Comil at less than 1,000 rpm, and then mixed with an osmotic agent previously milled using a Fitz Mill with a screen 0020-0069 at less than 8000 rpm, in a mixer granulator for up to 25 minutes to form a homogenous powder blend. The granulation process is initiated by adding a solution containing a plasticizer of low molecular weight and a plasticizer of higher molecular weight in purified water for granules. The wet granulation is sieved through a Quadro Comil at a speed less than 1000 rpm, and then dried in a static bed at 50° C. for humidity reduction. Next, the dry granules are milled using a Quadro Comil with a screen R991μ at less than 2,000 rpm for size reduction. Then, a mixture of a glidant and a lubricant, previously sieved through a 100-mesh screen, is added and mixed for about 15 minutes. The resulting mixture is compressed in a compressor with 8.0 mm diameter punches to form uncoated cores.

A semipermeable membrane composition is prepared as follows: cellulose ester, and a plasticizer of low molecular weight are blended in a mixture of solvents. The blend is sprayed onto the uncoated cores to obtain coated cores. The coated cores are then perforated with a laser equipment to form at least one passageway of 0.2-0.8 mm of diameter.

The immediate or rapid release composition (layer A) is prepared as follows: the ondansetron, filler 1, filler 2, the binder and half of the disintegrant are first individually screened in a rotary mill with a 991 μm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, lubricant, and the other half of the disintegrant, previously sieved through a 30-mesh screen, are added and mixed for about 5 minutes.

The extended release layer (layer B) composition is prepared as follows: quetiapine and the ER polymer are first individually screened in a rotary mill with a 991 μm screen, and then mixed with filler 1, filler 2 and the inorganic salt previously milled using a hammer mill with a 0020 screen, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, plasticizer, and lubricant, previously sieved through a 30-mesh screen, are added and mixed for about 5 minutes.

The multi-layered tablets are manufactured as follows: the IR/RR composition is loaded into the first hopper (first filled position) of the tableting machine, the ER composition is loaded into the second hopper (second filled position) of the tableting machine, and the osmotic cores are placed into the internal core dispenser. The die is first filled with 100-500 mg of IR/RR composition, and then the osmotic core is dispensed onto the first composition. After that the die is filled with 150-800 mg of ER composition and finally all the components are compressed to obtained the multi-layered tablets.

Example 6

The following procedure is used to prepare a multi-layered tablet comprising an osmotic device that provides lithium ER, and an external IR or RR quetiapine-containing layer and an external ER divalproex sodium-containing layer in stacked arrangement with respect to and on opposite sides of the osmotic core. An exemplary formulation is disclosed below.

| Ingredients/functional category | Amount (mg) |
|---|---|
| Osmotic device | |
| Core | |
| Lithium | 300 |
| Filler 1 | 20-100 |
| Binder | 10-30 |
| Glidant | 0.2-5 |
| Lubricant | 1-7 |
| Sodium Chloride | 0-150 |
| Filler 2 | 10-60 |
| Semipermeable Membrane | |
| Cellulose ester 1 | 0-30.0 |
| Cellulose ester 2 | 0-30.0 |
| Plasticizer | 0.3-1.5 |
| Dry Coating | |
| Layer A (IR/RR) | |
| Quetiapine | 100.0 |
| Filler 1 | 20.0-300.0 |
| Filler 2 | 20.0-300.0 |
| Binder | 5.0-50.0 |
| Disintegrant | 5.0-20.0 |
| Glidant | 0.2-5.0 |
| Lubricant | 1.0-5.0 |
| Layer B (ER) | |
| Divalproex Na | 250.0 |
| ER Polymer | 2.5-50.0 |
| Filler 1 | 50.0-200.0 |
| Filler 2 | 50.0-200.0 |
| Plasticizer | 25.0-100.0 |
| Inorganic salt | 2.5-50.0 |
| Glidant | 0.5-12.5 |
| Lubricant | 2.5-12.5 |

Lithium, filler 1, filler 2, and a binder, are first individually screened to a uniform size using a Quadro Comil at less than 500 rpm, and then mixed with sodium chloride previously milled using a Fitz Mill with a screen 0020-0069 at less than 8000 rpm, in a mixer granulator for up to 5 minutes to form a homogenous powder blend. The granulation process is initiated by the gradual addition of purified water to the powder blend, with continuous mixing, to change the consistency of the dry powder ingredients to granules. The wet granulation is sieved through a Quadro Comil at a speed less than 500 rpm, and then dried in a static bed at 50° C. for humidity reduction. Next, the dry granules are milled using a Quadro Comil with a screen R991μ at less than 2,000 rpm for size reduction. Then, a mixture of the glidant and the lubricant, previously sieved through a 60-mesh screen, is added and mixed for about 5 minutes. The resulting mixture is compressed in a compressor with 7-10 mm diameter punches to form uncoated cores.

A semipermeable membrane composition is prepared as follows: cellulose ester 1, cellulose ester 2, and the plasticizer of low molecular weight are blended in acetone and purified water. The blend is sprayed onto the uncoated cores to obtain coated cores. The semipermeable membrane weight range is approximately between 8 and 20 mg. The membrane coating of each core is then perforated with laser equipment to form at least one passageway of 0.2-0.8 mm through the semipermeable coat.

The immediate or rapid release composition (layer A) is prepared as follows: the quetiapine, filler 1, filler 2, the binder, and half of the disintegrant are first individually screened in a rotary mill with a 991 μm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, lubricant, and the other half of the disintegrant, previously sieved through a 30-mesh screen, are added and mixed for about 5 minutes.

The extended release layer (layer B) composition is prepared as follows: the divalproex Na and ER polymer are first individually screened in a rotary mill with a 991 μm screen, and then mixed with filler 1, filler 2, and the inorganic salt previously milled using a hammer mill with a 0020 screen, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, plasticizer, and lubricant, previously sieved through a 30-mesh screen, are added and mixed for about 5 minutes.

The multi-layered tablets are manufactured as follows: the IR/RR composition is loaded into the first hopper (first filled position) of the tableting machine, the ER composition is loaded into the second hopper (second filled position) of the tableting machine, and the osmotic cores are placed into the internal core dispenser. The die is first filled with 150-800 mg of IR/RR composition, and then the osmotic core is dispensed onto the first composition. After that the die is filled with 350-880 mg of ER composition and finally all the components are compressed to obtained the multi-layered tablets.

Example 7

The following procedure is used to prepare a multi-layered tablet comprising a matrix core (exemplary intermediate drug-containing composition) that provides amantadine ER, and an external IR or RR levodopa/carbidopa-containing layer and an external ER levodopa-containing layer in stacked arrangement with respect to and on opposite sides of the matrix core. An exemplary formulation is disclosed below.

| Ingredients/functional category | Amount (mg) |
| --- | --- |
| Matrix Core | |
| Amantadine HCl | 160 |
| Filler | 50.0-150.0 |
| CR Polymer | 1.0-20.0 |
| Glidant | 0.2-1.0 |
| Lubricant | 0.2-1.0 |
| Hydrophilic agent | 5.0-25.0 |
| Dry Coating | |
| Layer A (IR/RR) | |
| Levodopa | 100.0 |
| Carbidopa | 50.0 |
| Filler | 30.0-150.0 |
| Binder | 5.0-25.0 |
| Disintegrant | 5.0-15.0 |
| Glidant | 0.5-2.5 |
| Lubricant | 0.5-5.0 |
| Layer B (ER) | |
| Levodopa | 100.0 |
| ER Polymer | 1.0-15.0 |
| Filler | 50.0-150.0 |
| Plasticizer | 5.0-40.0 |
| Glidant | 0.1-5.0 |
| Lubricant | 0.5-5.0 |

Amantadine hydrochloride, the filler, and the CR polymer are first screened in a high shear granulator for up to 6-8 minutes to form a homogenous powder blend. The granulation process is initiated by the gradual addition of purified water to the powder blend, with continuous mixing, to change the consistency of the dry powder ingredients to granules. The wet granulation is sieved through a #10 mesh screen, and then dried in a fluid bed at 50° C. during 30-40 minutes for humidity reduction. Next, the dry granules are milled using a conic mill with a 040G screen for size reduction. Then, a mixture of the glidant, lubricant, previously sieved through a 60-mesh screen, and the hydrophilic agent are added and mixed for about 5 minutes. The resulting mixture is compressed in a rotary tablet press with 7-8 mm diameter punches to form the matrix cores.

The IR/RR composition (layer A) is prepared as follows: the levodopa, carbidopa, filler, binder and half of the disintegrant are first individually screened in a rotary mill with a 991 μm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a fluid bed at 40-60° C. for humidity reduction. Next, the dry granules are milled using a rotary mill with a 1575 μm screen at less than 1200 rpm for size reduction. Then, glidant, lubricant, and the other half of the disintegrant, previously sieved through a 30-mesh screen, are added and mixed for about 5 minutes to obtain the IR/RR composition.

The ER layer (layer B) composition is prepared as follows: the levodopa and ER polymer are first individually screened in a rotary mill with a 991 μm screen, and then mixed with the filler in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, plasticizer and lubricant, previously sieved through a 30-mesh screen, are added and mixed for about 5 minutes to obtain the ER layer composition.

The multi-layered tablets are manufactured as follows: the ER composition is loaded into the first hopper (first filled position) of the tableting machine, the IR/RR composition is loaded into the second hopper (second filled position) of the tableting machine, and the matrix cores are placed into the internal core dispenser. The die is first filled with 150-320 mg of ER composition, and then the matrix core is dispensed onto the first composition. After that the die is filled with 190-350 mg of IR/RR composition, and finally all the components are compressed to obtained the multi-layered tablets.

Example 8

The following procedure is used to prepare a multi-layered tablet comprising a capsule (exemplary intermediate drug-containing composition) containing venlafaxine CR micro-osmotic tablets, and an external IR or RR ondansetron-containing layer and an external ER alprazolam-containing layer in stacked arrangement with respect to and on opposite sides of the capsule. An exemplary formulation is disclosed below.

| Ingredients/functional category | Amount (mg) |
| --- | --- |
| Hard gelatin capsule | 7 micro-osmotic tablets per capsule |
| Micro-osmotic tablet | |
| Core | |
| Venlafaxine Hydrochloride | 24.25 |
| Osmotic agent | 3.0-14.0 |
| Binder | 1.5-5.0 |
| Plasticizer | 0.7-1.4 |
| Glidant | 0.1-0.8 |
| Lubricant | 0.2-0.8 |
| Membrane | |
| Cellulose ester | 4.0-9.0 |
| Plasticizer | 0.3-0.9 |
| Dry Coating | |
| Layer A (IR/RR) | |
| Ondansetron HCl•2H2O | 5.0 |
| Filler | 50.0-200.0 |
| Binder | 5.0-30.0 |
| Disintegrant | 2.0-10.0 |
| Glidant | 0.5-3.0 |
| Lubricant | 0.5-4.0 |
| Layer B (ER) | |
| Alprazolam | 1.0 |
| ER Polymer | 5.0-20.0 |
| Filler 1 | 20.0-100.0 |
| Filler 2 | 20.0-150.0 |
| Plasticizer | 10.0-30.0 |
| Inorganic Salt | 2.0-20.0 |
| Glidant | 0.1-5.0 |
| Lubricant | 1.0-5.0 |

Venlafaxine hydrochloride, the osmotic agent, and the binder, are mixed in a mixer granulator to form a homogenous powder blend. The granulation process is initiated by adding a solution of plasticizer in purified water to the powder blend. The wet granulation is then dried at 40-50° C. for 3 hours. Next, the dry granules are screened and then mixed with the glidant and the lubricant, previously sieved through a 100-mesh screen. The resulting mixture is compressed in a compressor with 3.0-4.0 mm diameter punches to obtain micro-tablets of 34-50 mg each.

A membrane composition is prepared as follows: cellulose ester, and the plasticizer are blended in a mixture of solvents. The blend is sprayed onto the micro-tablets to obtain the micro-osmotic tablets. Hard gelatin capsules are filled with 7 micro-osmotic tablets per capsule.

The immediate or rapid release composition (layer A) is prepared as follows: the ondansetron, the filler, the binder, and half of the disintegrant are first individually screened in a rotary mill with a 991 μm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a fluid bed at 40-60° C. for humidity reduction. Next, the dry granules are milled using a rotary mill with a 1575 μm screen at less than 1200 rpm for size reduction. Then, glidant, lubricant and the other half of the disintegrant, previously sieved through a 30-mesh screen, are added and mixed for about 5 minutes.

The extended release layer (layer B) composition is prepared as follows: alprazolam and the ER polymer are first individually screened in a rotary mill with a 991 μm screen, and then mixed with the filler 1, filler 2, and the inorganic salt previously milled using a hammer mill with a 0020 screen, in a mixer granulator for up to 10 minutes to form a homogenous powder blend. The granulation process was initiated by the gradual addition of purified water to the powder blend, with continuous mixing, to change the consistency of the dry powder ingredients to granules. The wet granulation is dried in a fluid bed at 40-60° C. for humidity reduction. Next, the dry granules are milled using a rotary mill with a 1575 μm screen at less than 1200 rpm for size reduction. Then, the glidant, plasticizer and lubricant, previously sieved through a 30-mesh screen, are added and mixed for about 5 minutes.

The multi-layered tablets are manufactured as follows: the IR/RR composition is loaded into the first hopper (first filled position) of the tableting machine, the ER composition is loaded into the second hopper (second filled position) of the tableting machine, and the hard gelatin capsules are placed into the internal dispenser. The die is first filled with 60-255 mg of IR/RR composition, and then the hard gelatin capsule is dispensed onto the first composition. After that the die is filled with 60-350 mg of ER composition and finally all the components are compressed to obtained the multi-layered tablets.

Example 9

The following procedure is used to prepare a multi-layered tablet comprising a gastro-resistant coated core that provides a delayed and extended release of levodopa, and an external IR or RR carbidopa-containing layer and an external ER entacapone-containing layer in stacked arrangement with respect to and on opposite sides of the gastro-resistant coated core. An exemplary formulation is disclosed below.

| Ingredients/functional category | Amount (mg) |
|---|---|
| Gastro-resistant coated core | |
| Core (ER) | |
| Levodopa | 200.0 |
| Filler | 10.0-200.0 |
| CR polymer | 2.0-40.0 |
| Glidant | 0.4-10 |
| Lubricant | 2.0-10.0 |
| Enteric coating (DR) | |
| Enteric film polymer | 5.0-200.0 |
| Plasticizer (optional) | 0.1-20.0 |
| Plasticizer | 0.3-1.5 |
| Dry Coating | |
| Layer A (IR/RR) | |
| Carbidopa | 50.0 |
| Filler 1 | 20.0-150.0 |
| Filler 2 | 20.0-150.0 |
| Binder | 5.0-50.0 |
| Disintegrant | 5.0-20.0 |
| Glidant | 0.2-5.0 |
| Lubricant | 1.0-5.0 |
| Layer B (ER) | |
| Entacapone | 200.0 |
| CR Polymer | 1.0-15.0 |
| Filler 1 | 20.0-300.0 |
| Filler 2 | 20.0-300.0 |
| Plasticizer | 10.0-50.0 |
| Inorganic salt | 1.0-30.0 |
| Glidant | 0.2-5.0 |
| Lubricant | 1.0-5.0 |

The ER core composition is prepared as follows: the levodopa and CR polymer are first individually screened in a rotary mill with a 991 μm screen, and then mixed with filler, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant and the lubricant, previously sieved through a 30-mesh screen, are added and mixed for about 5 minutes. The final blend is tabletted to provide the cores.

The enteric coating composition is prepared as follows: the enteric film polymer, and the plasticizer are blended in purified water to form a polymer suspension. This suspension is sprayed onto the cores in a perforated pan coater to obtain gastro-resistant coated cores.

The IR/RR composition (layer A) is prepared as follows: carbidopa, filler 1, filler 2, binder, and half of the disintegrant are first individually screened in a rotary mill with a 991 μm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, lubricant, and the other half of the disintegrant, previously sieved through a 30-mesh screen, are added and mixed for about 5 minutes to obtain the IR/RR composition.

The ER layer (layer B) composition is prepared as follows: entacapone and the CR polymer are first individually screened in a rotary mill with a 991 μm screen, and then mixed with filler 1, filler 2 and inorganic salt previously milled using a hammer mill with a 0020 screen, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 μm screen at less than 1200 rpm for size reduction. Then, the glidant, plasticizer, and lubricant, previously sieved through a 30-mesh screen, are added and mixed for about 5 minutes to obtain the ER composition.

The multi-layered tablets are manufactured as follows: the IR/RR composition is loaded into the first hopper (first filled position) of the tableting machine, the ER composition is loaded into the second hopper (second filled position) of the tableting machine, and the dry gastro-resistant coated cores are placed into the internal core dispenser. The die is first filled with 100-430 mg of IR/RR composition, and then the gastro-resistant coated core is dispensed onto the first composition. After that the die is filled with 250-900 mg of ER composition and finally all the components are compressed to obtained the multi-layered tablets.

Example 10

The following procedure is used to prepare a multi-layered tablet comprising a gastro-resistant coated core that provides a delayed and extended release of levodopa, and an external IR or RR levodopa/carbidopa-containing layer and an external ER entacapone-containing layer in stacked arrangement with respect to and on opposite sides of the gastro-resistant coated core. An exemplary formulation is disclosed below.

| Ingredients/functional category | Amount (mg) |
|---|---|
| Gastro-resistant coated core | |
| Core (ER) | |
| Levodopa | 100.0 |
| Filler | 5.0-100.0 |
| CR polymer | 1.0-20.0 |
| Glidant | 0.2-5.0 |
| Lubricant | 1.0-5.0 |
| Enteric coating (DR) | |
| Enteric film polymer | 5.0-200.0 |
| Plasticizer (optional) | 0.1-20.0 |
| Plasticizer | 0.3-1.5 |
| Dry Coating | |
| Layer A (IR/RR) | |
| Levodopa | 100.0 |
| Carbidopa | 50.0 |
| Filler 1 | 20.0-300.0 |
| Filler 2 | 20.0-300.0 |
| Binder | 5.0-50.0 |
| Disintegrant | 5.0-20.0 |
| Glidant | 0.2-5.0 |
| Lubricant | 1.0-5.0 |
| Layer B (ER) | |
| Entacapone | 200.0 |
| CR Polymer | 1.0-15.0 |
| Filler 1 | 20.0-300.0 |
| Filler 2 | 20.0-300.0 |

| Ingredients/functional category | Amount (mg) |
|---|---|
| Plasticizer | 10.0-50.0 |
| Inorganic salt | 1.0-30.0 |
| Glidant | 0.2-5.0 |
| Lubricant | 1.0-5.0 |

The ER core composition is prepared as follows: the levodopa and CR polymer are first individually screened in a rotary mill with a 991 µm screen, and then mixed with filler, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 µm screen at less than 1200 rpm for size reduction. Then, the glidant and the lubricant, previously sieved through a 30-mesh screen, are added and mixed for about 5 minutes. The final blend is tabletted to provide the cores.

The enteric coating composition is prepared as follows: the enteric film polymer, and the plasticizer are blended in purified water to form a polymer suspension. This suspension is sprayed onto the cores in a perforated pan coater to obtain gastro-resistant coated cores.

The IR/RR composition (layer A) is prepared as follows: the levodopa, carbidopa, filler 1, filler 2, binder, and half of the disintegrant are first individually screened in a rotary mill with a 991 µm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 µm screen at less than 1200 rpm for size reduction. Then, the glidant, lubricant, and the other half of the disintegrant, previously sieved through a 30-mesh screen, are added and mixed for about 5 minutes to obtain the IR/RR composition.

The ER layer (layer B) composition is prepared as follows: entacapone and the CR polymer are first individually screened in a rotary mill with a 991 µm screen, and then mixed with filler 1, filler 2 and inorganic salt previously milled using a hammer mill with a 0020 screen, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 µm screen at less than 1200 rpm for size reduction. Then, the glidant, plasticizer, and lubricant, previously sieved through a 30-mesh screen, are added and mixed for about 5 minutes to obtain the ER composition.

The multi-layered tablets are manufactured as follows: the IR/RR composition is loaded into the first hopper (first filled position) of the tableting machine, the ER composition is loaded into the second hopper (second filled position) of the tableting machine, and the dry gastro-resistant coated cores are placed into the internal core dispenser. The die is first filled with 200-830 mg of IR/RR composition, and then the gastro-resistant coated core is dispensed onto the first composition. After that the die is filled with 250-900 mg of ER composition and finally all the components are compressed to obtained the multi-layered tablets.

Example 11

The following procedure is used to prepare a multi-layered tablet comprising an osmotic device (intermediate drug-containing composition) that provides domperidone ER, and an external IR or RR ergotamine-containing layer and an external ER naproxen-containing layer in stacked arrangement with respect to and on opposite sides of the osmotic core. An exemplary formulation is disclosed below.

| Ingredients/functional category | Amount (mg) |
|---|---|
| Osmotic device | |
| Core | |
| Domperidone | 10 |
| Filler 1 | 50.0-200.0 |
| Binder | 5.0-20.0 |
| Glidant | 0.15-3.0 |
| Lubricant | 0.5-5.0 |
| Osmotic agent | 0-70 |
| Filler 2 | 50.0-150.0 |
| Semipermeable Membrane | |
| Cellulose ester 1 | 0-20.0 |
| Cellulose ester 2 | 0-20.0 |
| Plasticizer | 0.3-1.5 |
| Dry Coating | |
| Layer A (IR/RR) | |
| Ergotamine | 1.0 |
| Filler 1 | 50.0-350.0 |
| Filler 2 | 50.0-200.0 |
| Binder | 5.0-30.0 |
| Disintegrant | 5.0-25.0 |
| Glidant | 0.2-5.0 |
| Lubricant | 1.0-5.0 |
| Layer B (ER) | |
| Naproxen | 500.0 |
| ER Polymer | 1.0-150.0 |
| Filler 1 | 50.0-350.0 |
| Filler 2 | 50.0-200.0 |
| Inorganic salt | 1.0-30.0 |
| Glidant | 0.2-5.0 |
| Lubricant | 1.0-5.0 |

Domperidone, filler 1, filler 2, and a binder, are first individually screened to a uniform size using a Quadro Comil at less than 500 rpm, and then mixed with osmotic agent previously milled using a Fitz Mill with a screen 0020-0069 at less than 8000 rpm, in a mixer granulator for up to 5 minutes to form a homogenous powder blend. The granulation process is initiated by the gradual addition of purified water to the powder blend, with continuous mixing, to change the consistency of the dry powder ingredients to granules. The wet granulation is sieved through a Quadro Comil at a speed less than 500 rpm, and then dried in a static bed at 50° C. for humidity reduction. Next, the dry granules are milled using a Quadro Comil with a screen R991µ at less than 2,000 rpm for size reduction. Then, a mixture of a glidant and a lubricant, previously sieved through a 60-mesh screen, is added and mixed for about 5 minutes. The resulting mixture is compressed in a compressor with 6-10 mm diameter punches to form uncoated cores.

A semipermeable membrane composition is prepared as follows: cellulose ester 1, cellulose ester 2, and a plasticizer of low molecular weight are blended in acetone and purified water. The blend is sprayed onto the uncoated cores to obtain coated cores. The semipermeable membrane weight range is approximately between 10 and 40 mg. The coated cores are then perforated with a laser equipment to form at least one passageway of 0.2-0.8 mm of diameter.

The IR/RR composition (layer A) is prepared as follows: the ergotamine, filler 1, filler 2, binder and half of the disintegrant are first individually screened in a rotary mill with a 991 µm screen, and then mixed in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 µm screen at less than 1200 rpm for size reduction. Then, glidant, lubricant, and the other half of the disintegrant, previously sieved through a 30-mesh screen, are added and mixed for about 5 minutes to obtain the IR/RR composition.

The ER layer (layer B) composition is prepared as follows: the naproxen and ER polymer are first individually screened in a rotary mill with a 991 µm screen, and then mixed with filler 1, filler 2 and inorganic salt previously milled using a hammer mill with a 0020 screen, in a mixer granulator for up to 10 minutes to form a homogenous powder blend. The granulation process is initiated by the gradual addition of purified water to the powder blend, with continuous mixing, to change the consistency of the dry powder ingredients to granules. The wet granulation is dried in a static bed at 50-70° C. or in a fluid bed at 40-60° C. for humidity reduction. Next, the dry granules are milled using a rotary mill with a 1575 µm screen at less than 1200 rpm for size reduction. Then, the glidant and lubricant, previously sieved through a 60-mesh screen, are added and mixed for about 5 minutes to obtain the ER layer composition.

The multi-layered tablets are manufactured as follows: the IR/RR composition is loaded into the first hopper (first filled position) of the tableting machine, the ER composition is loaded into the second hopper (second filled position) of the tableting machine, and the osmotic cores are placed into the internal core dispenser. The die is first filled with 150-550 mg of IR/RR composition, and then the osmotic core is dispensed onto the first composition. After that the die is filled with 150-900 mg of ER composition and finally all the components are compressed to obtained the multi-layered tablets.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

The invention claimed is:

1. A combination release tablet comprising:
   a) a drug-containing rapid release first compressed composition comprising at least one drug, a first filler and a second filler;
   b) a drug-containing extended release second compressed composition comprising at least one drug, release rate modifier, the first filler and the second filler; and
   c) a film-coated extended release intermediate drug-containing composition enclosed between the first compressed composition and the second compressed composition and comprising a drug-containing core surrounded by a film coating; wherein the first compressed composition and second compressed composition oppose one another, are in direct contact with each other, and are in direct contact with, in stacked arrangement with respect to, and disposed on opposite faces or surfaces of the intermediate drug-containing composition, wherein the preformed and film-coated extended release intermediate drug-containing composition is an osmotic device comprising a core surrounded by a membrane having a preformed passageway through it, wherein the preformed passageway is plugged by the first or second compressed composition and initial release of drug from the core after administration is delayed, whereby the tablet provides three different active agent release profiles.

2. The tablet of claim 1, wherein the first compressed composition comprises binder.

3. The tablet of claim 2, wherein the first compressed composition further comprises disintegrant.

4. The tablet of claim 1, wherein the first filler and the second filler are selected from the group consisting of: dibasic calcium phosphate, kaolin, lactose, sucrose, mannitol, microcrystalline cellulose, powdered cellulose, precipitated calcium carbonate, sorbitol, and starch.

5. The tablet of claim 4, wherein the release rate modifier is selected from the group consisting of water-soluble natural polymers, water-soluble semi-synthetic polymers and water-soluble synthetic polymers.

6. The tablet of claim 4, wherein the release rate modifier is selected from the group consisting of: a) natural polymer selected from the group consisting of polysaccharide and polypeptide; b) semi-synthetic polymer selected from the group consisting of cellulose derivatives; and c) synthetic polymer selected from the group consisting of polyoxyethylene derivatives, polyvinyl derivatives, copolymer of acrylic acid or ester, and copolymer of methacrylic acid or ester.

7. The tablet of claim 6, wherein: a) the polysaccharide is inulin, pectin, algin derivative or agar; b) the polypeptide is casein or gelatin; c) the semi-synthetic polymers is a cellulose derivative; d) the polyoxyethylene derivative is polyethylene glycol; or e) the polyvinyl derivative is polyvinyl alcohol, polyvinylpyrrolidone or polystyrene sulfonate.

8. The tablet of claim 7, wherein the cellulose derivative is methylcellulose, hydroxyethylcellulose, hydroxypropyl cellulose, hydroxypropyl methylcellulose, hydroxyethyl ethylcellulose, hydroxypropyl ethylcellulose, hydroxypropyl methylcellulose phthalate or carboxymethylcellulose.

9. The tablet of claim 4, wherein the release rate modifier is selected from the group consisting of hydroxypropyl methylcellulose, hydroxypropylcellulose, poly(ethylene oxide), cellulose acetate butyrate, cellulose acetate propionate, cellulose propionate, carrageenan, cellulose acetate, cellulose nitrate, methylcellulose, hydroxyethyl cellulose, ethylcellulose, polyvinyl acetate, latex dispersions, acacia, tragacanth, guar gum, gelatin, wax, and a combination thereof.

10. The tablet of claim 1, wherein the membrane is a semipermeable membrane, a microporous membrane, or an impermeable membrane.

11. The tablet of claim 1, wherein the tablet comprises three different drugs.

12. The tablet of claim 11, wherein a drug in the first compressed composition is different than a drug in the second compressed composition.

13. The tablet of claim 12, wherein a drug in the first compressed composition is different than a drug in the drug-containing core.

14. The tablet of claim 12, wherein the drug in the second compressed composition is different than the drug in the drug-containing core.

15. The tablet of claim 11, wherein the drug in the first compressed composition is the same as the drug in the drug-containing core.

16. The tablet of claim 11, wherein the first compressed composition comprises two different drugs, the core comprises the third different drug, and the second compressed composition comprises a charge of either one of the three different drugs.

17. The tablet of claim 11, wherein the first compressed composition comprises a charge of each of two different drugs, the core comprises a charge of the third different drug, and the second compressed composition comprises an additional charge of either one of the three different drugs.

18. The tablet of claim 11, wherein the drug in the first compressed composition is the same as the drug in the second compressed composition.

19. The tablet of claim 18, wherein the drug in the first compressed composition is the same as the drug in the drug-containing core.

20. The tablet of claim 18, wherein the drug in the second compressed composition is different than the drug in the drug-containing core.

* * * * *